United States Patent [19]

Holt et al.

[11] Patent Number: 5,026,882

[45] Date of Patent: Jun. 25, 1991

[54] PHOSPHINIC ACID SUBSTITUTED STEROIDS AS INHIBITORS OF STEROID 5 ALPHA-REDUCTASE

[75] Inventors: Dennis A. Holt, Downingtown; Mark A. Levy, Wayne; Brian W. Metcalf, Radnor, all of Pa.

[73] Assignee: SmithKline Beecham Corporation, Philadelphia, Pa.

[21] Appl. No.: 290,212

[22] Filed: Dec. 23, 1988

[51] Int. Cl.$^5$ .................. C07J 53/00; C07J 71/00; C07J 43/00; A01N 59/26

[52] U.S. Cl. .................. 552/506; 552/507; 424/601; 540/5; 540/23; 540/95; 540/100

[58] Field of Search .................. 424/601; 540/5, 23, 540/95, 100; 200/397, 397.5; 552/506, 507

[56] References Cited

U.S. PATENT DOCUMENTS 4,191,759  3/1980  Johnston et al. .................. 514/177
4,317,817  3/1982  Blohm et al. .................. 514/150
4,361,578  11/1982 Alig et al. .................. 514/162
4,377,584  3/1983  Rasmusson et al. .................. 514/284

OTHER PUBLICATIONS

Hsia and Voight, J. Invest, Dermat, 62:224–227 (1973).
Robaire et al., J. Steroid Biochem. 8:307–310 (1977).
Blohm, T. R., et al., Biochem. Biophys. Res. Comm. 95:273–280 (1980).
Liang, T., et al., J. Steroid Biochm. 19, 385–390 (1983).
Petrow, V., et al., Steroids 38:121–140 (1982).
Brooks et al., Steroids: 47:1–19 (Jan. 1986).

Primary Examiner—Stanley J. Friedman
Assistant Examiner—Theodore J. Criares
Attorney, Agent, or Firm—Wayne J. Dustman; Stuart R. Suter; Edward T. Lentz

[57] ABSTRACT

The invention relates to 3-phosphinic acid steroidal compounds, pharmaceutical compositions containing these compounds, and methods of using these compounds to inhibit steroid 5α-reductase.

20 Claims, No Drawings

PHOSPHINIC ACID SUBSTITUTED STEROIDS AS INHIBITORS OF STEROID 5 ALPHA-REDUCTASE

FIELD OF THE INVENTION

The present invention relates to steroid 3 phosphinic acid compounds, pharmaceutical compositions containing these compounds, and methods for using these compounds to inhibit mammalian steroid 5α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifastations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the primary androgenic steroid in the plasma of males. It now is known that 5α-reduced androgens are the active hormones in some tissues such as the prostate and sebaceous gland. Circulating testosterone thus serves as a prohormone for dihydrotestosterone (DHT), its 5α-reduced analogue in these tissues but not in others such as muscle and testis. Steroid 5α-reductase is an NADPH dependent enzyme that converts testosterone to DHT. The importance of this enzyme in male development was dramatically underscored by discovery of a genetic steroid 5α-reductase deficiency in male pseudohermaphrodites. Imperato McGinley, J., et al., (1979), *J. Steroid Biochem.* 11 :637-648.

Recognition of the importance of elevated DHT levels in many disease states has stimulated many efforts to synthesize inhibitors of this enzyme. The structures of several known steroid 5α-reductase inhibitors are shown in Table 1.

TABLE 1

| COMPOUND | 5α-Reductace Inhibitors $K_i$ | REFERENCE |
|---|---|---|
| 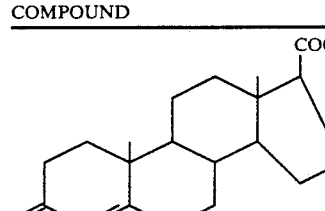 (1) | $1.1 \times 10^{-6}$ M (Reversible) | Hsia and Voight 1973 |
| (2) 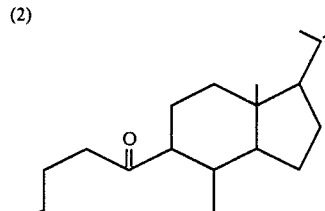 | $1 \times 10^{-6}$ M (Irreversible) | Robaire, et al., 1977 |
| (3) 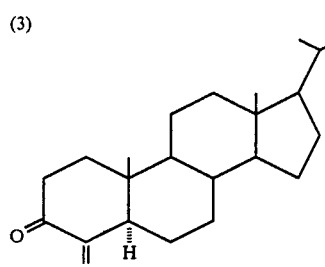 | $3.5 \times 10^{-9}$ M (Irreversible) | Blohm, et al., 1980 |
| (4) 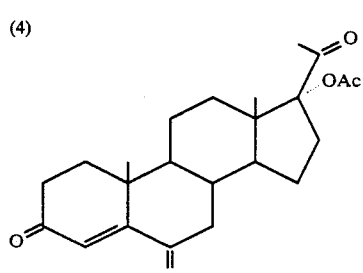 | $5 \times 10^{-9}$ M (Reversible) | Liang, et al., 1983 |

TABLE 1-continued

5α-Reductace Inhibitors

| COMPOUND | $K_i$ | REFERENCE |
|---|---|---|
| (5) [structure] | $1.25 \times 10^{-6}$ M (Irreversible) | Petrow, et al., 1981 |

The first inhibitor described was the 17β-carboxylic acid (1) by Hsia and Voight in 1973. *J. Invest. Dermat.* 62:224–227. The secosteroid (2) was the next inhibitor to be described and also has found utility as an affinity label for 5α-reductase. Robaire, B., et al., (1977) *J. Steroid Biochem.* 8:307–310. The diazoketone (3) has been reported as a potent, time-dependent inhibitor of steroid 5α-reductase. Blohm, T. R., et al. (1980), *Biochem. Biophys. Res. Comm.* 95:273–280; U.S. Pat. No. 4,317,817, Mar. 2, 1982. Compound (4) is exemplary of a group of 4-aza steroid inhibitors of steroid 5α-reductase described in U.S. Pat. No. 4,377,584 which issued Mar. 22, 1983, and in Liang, T., et al. (1983), *J. Steroid Biochem.* 19, 385–390. The 6-methylene steroid (5) also has been shown to be a time dependent inactivator of steroid 5α-reductase. Petrow, V., et al. (1981), *Steroids* 38:121–140.

Other steroid 5α-reductase inhibitors also have been described. U.S. Pat. No. 4,361,578 which issued June 2, 1986, describes a class of homosteroid enzyme inhibitors. U.S. Pat. No. 4,191,759 discloses amides of 17β-carboxy 4-androsten-3-one that are active as steroid 5α-reductase inhibitors. Japanese Patents J60146855-A and J60116657-A disclose various aniline derivatives having numerous activities including 5α-reductase inhibiting activity. Japanese Patent I60142941-A discloses phenyl-substituted ketones having 5α-reductase inhibiting activity and European Patent EP 173516-A discloses various phenyl substituted amides having similar activity. Shiseido referenced terpene derivatives that are active inhibitors of steroid 5α-reductase. Japanese Patent No. J59053417-A.

Zeches, M. et al, *Eur. J. Med. Chem. —Chemica Therapeutica,* 10:309–314 (1975) reported on 3-phosphinic acid derivatives of testosterone, progesterone and cholestenone. The steroidal-3-phosphinic acid compounds of the present invention differ in the 17-position from the testosterone, progesterone and cholestenone compounds

SUMMARY OF THE INVENTION

The present invention resides in the discovery that steroid 5α-reductase is inhibited by certain steroidal-3-phosphinic acid compounds. The compounds are potent enzyme inhibitors.

Presently preferred compounds of the invention are compounds used in the invented pharmaceutical compositions and the invented methods include:

17β-(N,N-diisopropylcarboxamide) androst-3,5-diene-phosphinic acid,
17β-(N-t-butylcarboxamide)-androst-3,5-diene-3-phosphinic acid,
17β-(N,N-diisopropylcarboxamide) 5α-androst-3-ene-3-phosphinic acid,
17β-(N,N-diisopropylcarboxamide) 5α-androst-2-ene-3-phosphinic acid,
17β-(N,N-diisopropylcarboxamide androst-2,4-diene-3-phosphinic acid, and
Methyl (17β-N,N-diisopropylcarboxamide) androst-3,5-diene-3-phosphinic acid.

Other compounds of the invention include, but are not limited to, the following:
20α-(hydroxymethyl) 5α-pregn-3-ene3-phosphinic acid,
17β-(N,N-diisopropylcarboxamide)-4-fluoro5α-androst-3-ene-3-phosphinic acid,
20α-(hydroxymethyl)-4-fluoro-5α-pregn-3-ene-phosphinic acid,
20α-(hydroxymethyl)-A-nor-5α-pregn-1-ene-2-phosphinic acid,
17β-(N,N-diisopropylcarboxamide)-5α-androst-1,3-diene-3-phosphinic acid,
17α-(N,N-diisopropylcarboxamide)-5α-androstane-3α-phosphinic acid,
17α-(N,N-diisopropylcarboxamide)-estr-3,5(10)-diene-3-phosphinic acid,
17β-(N,N-Diisoproplycarboxamide)-estr-3,5-diene-phosphinic acid,
17β-(N,N-Diisoproplycarboxamide)-androst-3,5-11-triene-3-phosphinic acid.

In a further aspect of the invention there are provided novel $C_{1-18}$ alkyl phosphinate esters which are useful as intermediates in preparing the phosphinic acids of this invention and are also useful as prodrugs. Exemplary of the esters is 17β-(N,N-diisopropylcarboxamide) androst-3,5-diene-3-phosphinic acid methyl The invention also relates to a method for inhibiting 5α-reductase activity in mammals, including humans, that comprises administering to a subject in need thereof an effective amount of a presently invented reductase inhibiting compound.

Included in the present invention are pharmaceutical compositions comprising a pharmaceutical carrier and compounds useful in the methods of the invention.

DETAILED DESCRIPTION OF THE INVENTION

The phosphinic acid compounds of this invention tha inhibit steroid 5α-reductase have the following Formula (I):

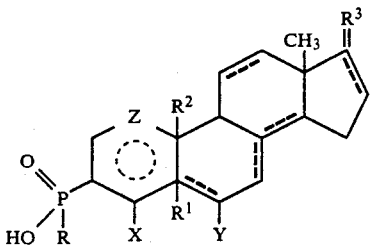

in which:

The A ring has up to 2 double bonds;

The B, C, and D rings have optional double bonds where indicated by the broken lines, provided that the A, B and C rings do not have adjacent double bonds;

R is hydrogen or $C_{1-4}$ alkyl;

Z is $(CH_2)_n$ and n is 0-2;

X is H, F, Cl, Br, I, $CF_3$, or $C_{1-6}$ alkyl;

Y is H, F, Cl, $CF_3$, or $CH_3$, provided that Y is H when there is no $C_5-C_6$ double bond;

$R^1$ is absent or present as an alpha hydrogen provided $R^1$ is absent when there is a $C_4-C_5$, $C_5-C_6$, or $C_5-C_{10}$ double bond;

$R^2$ is absent or present as H or $CH_3$, provided $R^2$ is absent when the carbon to which it is attached is double bonded; and $R^3$ is (1) α-hydrogen, α-hydroxyl, or α-acetoxy and/or (a)

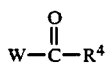

where W is a bond or $C_{1-12}$ alkyl and $R^4$ is (i) hydrogen, (ii) hydroxyl, (iii) $C_{1-8}$alkyl (iv) $C_{1-8}$ alkoxy, (v) $N(R^5)_2$, where each $R^5$ is each independently selected from hydrogen, $C_{1-8}$-alkyl, $C_{3-6}$cycloalkyl, phenyl; or taken together with the nitrogen to which they are attached represent a 5-6 membered saturated ring comprising up to one other heteroatom selected from oxygen and nitrogen, or (vi) $OR^6$, where $R^6$ is hydrogen, alkali metal, $C_{1-8}$alkyl, benzyl, or (b) Alk $OR^7$, where Alk is $C_{1-12}$alkyl, and $R^7$ is (i) phenyl$C_{1-6}$alkylcarbonyl, (ii) $C_{5-10}$cycloalkylcarbonyl, (iii) benzoyl, (iv) $C_{1-8}$alkoxycarbonyl, (v) amino carbonyl or $C_{1-8}$alkyl substituted amino carbonyl, (vi) hydrogen, or (vii) $C_{1-8}$alkyl, (2) =CH—W—CO—$R^4$ or =CH—W—$OR^7$, where W is a bond or $C_{1-12}$ alkyl, and $R^4$ and $R^7$ have the same meaning as above and $R^7$ also s hydrogen or $C_{1-20}$alkycarbonyl;

(3)

where the dashed bond replaces the 17α-hydrogen, (4) α-hydrogen and $NHCOR^8$ where $R^8$ is where is $C_{1-12}$alkyl or $N(R^5)_2$ where $R^5$ has the same meaning as above, (5) α-hydrogen and cyano, (6) α-hydrogen and tetrazolyl, or (7) keto;

or a pharmaceutically acceptable salt thereof.

As used herein, unless otherwise specified, $C_{1-m}$alkyl and $C_{1-m}$alk means a straight or branched hydrocarbon chain having 1 to n' carbons and Alk means a straight or branched hydrocarbon chain having 1 to 12

Preferred among Formula (I) compounds are those in which Z is —$CH_2$—.

Among preferred compounds of Formula (I) are those in which $R^3$ is N,N-diisopropylcarboxamide or N-t-butylcarboxamide.

Also, preferred among the presently invented compounds are those having Formula (II):

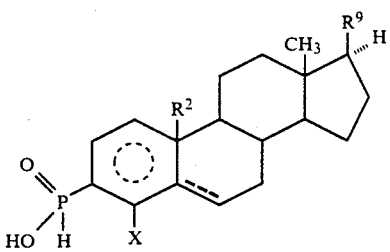

in which:

The A ring has up to 2 double bonds;

The B ring has an optional double bond where indicated by the broken line and provided that the A and B rings do not have adjacent double bonds;

X is H, or halo, and $R^9$ is (a) $C(CH_3)CH_2OR^{10}$ wherein $R^{10}$ is H or $C_{1-6}$alkyl, or (b) $CON(R^{10})_2$ wherein $R^{10}$ is as defined above.

Particularly preferred are Formula (II) compounds in which the A ring has a $C_3-C_4$ double bond.

Also preferred among the presently invented compounds are those having Formula (III):

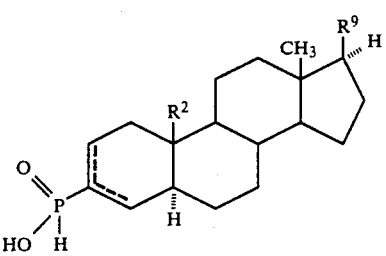

in which $R^2$ and $R^9$ are as in Formula (II) and the A has one double bond.

Additionally, preferred among the presently invented compounds are those having Formula (IV):

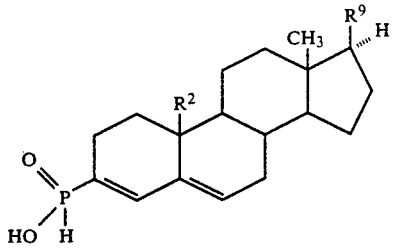
(IV)

in which $R^2$ and $R^9$ are as in Formula (II).

Compounds of Formula (I) are included in the pharmaceutical compositions of the invention and used in the methods of the invention.

Also included in this invention are the $C_{1-8}$ phosphinates of the formula

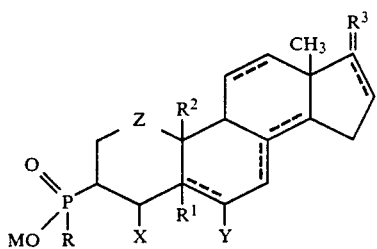
(Ia)

in which:
M is $C_{1-8}$alkyl;
R is hydrogen or $C_{1-4}$alkyl;
Z is $(CH_2)_n$ and n is 0-14 2; and
the A, B, C and D ring double bonds, Z, Z, Y, $R^1$, $R^2$ and $R^3$ are as defined in Formula (I).

As used above and throughout the remainder of the specification and claims the carbons of the steroid nucleus are numbered and the rings are lettered as follows:

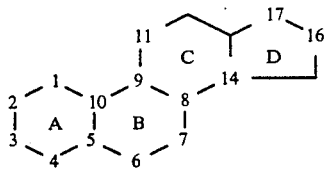

Formula (I) and (a) compounds are prepared as shown in Schemes I through IX wherein $R^2$ and X are as defined in Formula (I). R' is $R^3$ or moieties which can be chemically converted to those of $R^3$ by known chemical reactions such as described in J. Fried and J. Edwards, *Organic Reactions in Steroid Chemistry*, Pub: Van Nostrand Reinhold Company (1972) provided that R' does not include any such moities that render inoperative the Schemes I to IX processes. As demonstrated in the following Examples, reactions to convert R' to $R^3$ are performed on products of the synthetic pathways of Schemes I through IX or, where appropriate or preferable, on certain intermediates in these synthetic pathways.

SCHEME I

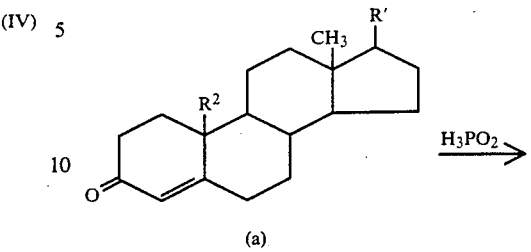
(a)

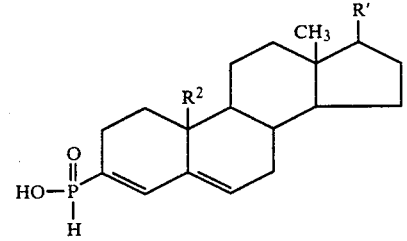

According to Scheme I, compounds of Formula I have double bonds at $C_3-C_4$ and $C_5-C_6$ are prepared from 4-ene-3-one compounds, formula (a). The formula (a) starting materials are known or readily available and are synthesized from available precursors using known procedures. The 4-ene-3-one starting materials are dissolved in an appropriate organic solvent such as dimethylformamide and treated with hypophosphorous acid in an inert atmosphere such as argon. The reaction mixture is stirred at about 50°–100° C., preferably 65° C., for about 24–48 hours to provide the 3,5-diene-3-phosphinic acids.

SCHEME II

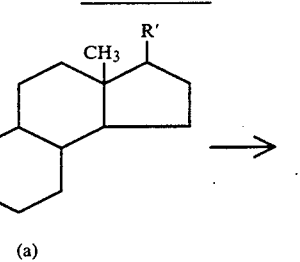
(a)

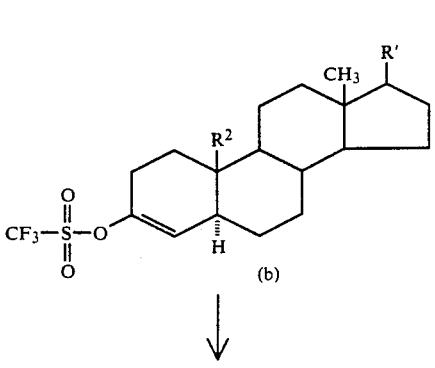
(b)

-continued
SCHEME II

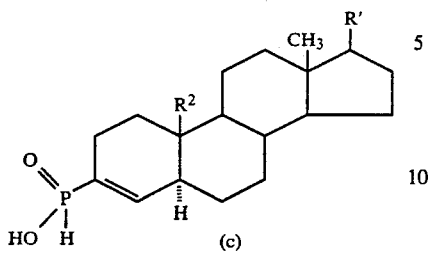

(c)

Scheme II depicts formation of Formula (I) compounds having a double bond at $C_3$–$C_4$, X is H, and n is 1. According to Scheme II, a solution of a 4-ene 3-one compound (a) and a suitable organic proton donor such as t-butanol, or, preferably aniline in an appropriate organic solvent, such as tetrahydrofuran (THF) are added to a reducing metal amine, such as a lithium/ammonia ($Li/NH_3$) solution, to form a reaction mixture. This reaction mixture is stirred at $-100°$ C. to $-30°$ C., preferably $-78°$ C., quenched with a lithium scavenger such as dibromoethane, bromobenzene, or, preferably isoprene, and evaporated to form a residue. Formula (b) compounds then are prepared by reacting the residue dissolved in a suitable organic solvent, such as THF, with an N-aryltrihaloalkylsulfonimide such as N phenyltrifluoro methylsulfonimide at a temperature of $-20°$ C. to $20°$ C.

Formula (c) compounds are prepared by adding to a formula (b) compound dissolved in a suitable organic solvent such as dimethylformamide (DMF), an organic base such as trimethylamine or triethylamine, tetrakis-(triphenylphosphine)palladium (0) and hypophosphorous acid.

SCHEME III

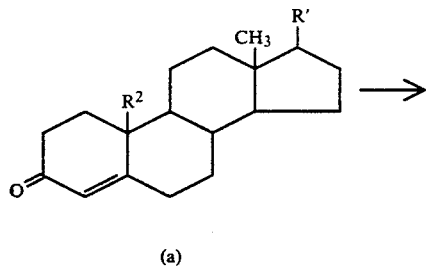

(a)

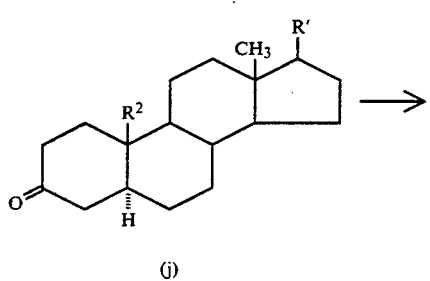

(j)

-continued
SCHEME III

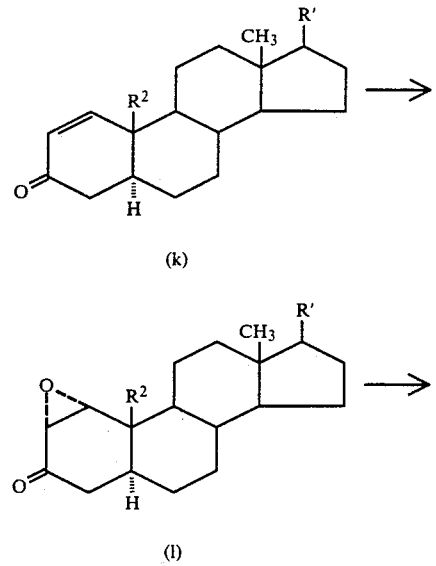

(k)

(l)

(m)

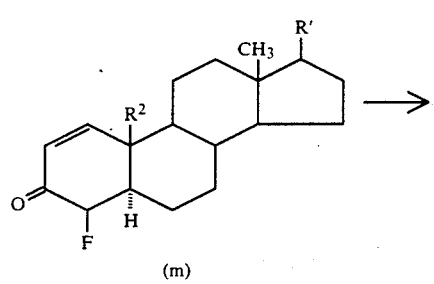

(o)

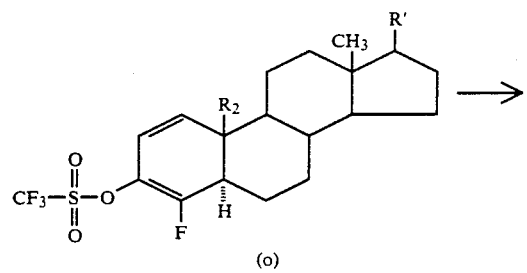

(p)

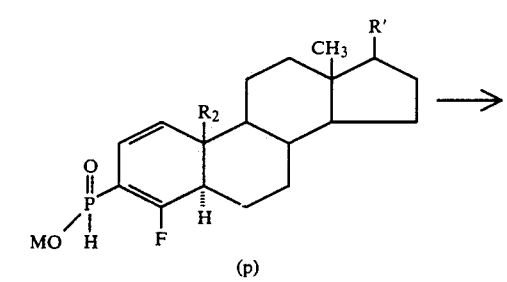

(q)

-continued
SCHEME III

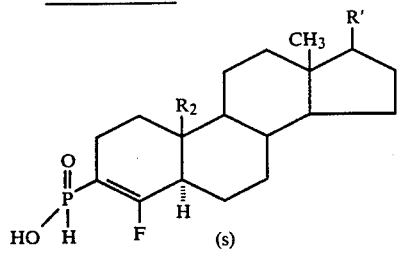

Scheme III illustrates synthesis of phosphinic acids and alkyl esters of this invention in which X is fluoro. The starting compounds are the 4-ene-3-one compounds (a) used in Schemes I and II. According to Scheme III, formula (a) compounds dissolved in a suitable organic solvent such as THF and t butyl alcohol are added to a metal/amine solution such as a $Li/NH_3$ solution, to form a reaction mixture which is cooled to $-100°$ C. to $-30°$ C., preferably $-78°$ C., and quenched with a lithium scavenger agent such as dibromoethane, bromobenzene, or preferably, isoprene to form an enolate. This enolate then is treated with a salt of a strong acid and base such as ammomium chloride ($NH_4Cl$), to yield a formula (j) compound. Addition of phenylselenyl chloride to a formula (j) compound dissolved in a suitable organic solvent such as ethyl acetate, followed by addition of an oxidizing agent such as hydrogen peroxide ($H_2O_2$), yields a formula (k) compound. The formula (1) epoxide compounds next are prepared by addition of an oxidizing agent such as $H_2O_2$, to formula (k) compound dissolved in a suitable organic solvent such as methanol, cooled to $5°$ C. to $25°$ C. such as $15°$ C., followed by addition of a strong base such as NaOH.

Formula (1) compounds then are dissolved in a suitable organic solvent such as THF, and cooled to $-20°$ C. to $0°$ C., and a fluorinating agent such as hydrogen fluoride, or pyridinium poly(hydrogen fluoride) is added to yield formula (m) compounds in which X is fluoro. Formula (m) compounds are dissolved in a suitable organic solvent such as THF followed by addition to a solution of a metalloamide base such as lithium diisopropylamide or lithium bis(trimethylsilyl)amide in a suitable organic solvent such as THF. To this reaction mixture is then added a triflating agent such as triflurormethanesulfonic anhydride, or N-phenyltrifluoromethanesulfonimide to yield formula (o) compounds.

Formula (p) compounds then are synthesized by formula (o) compounds by the procedure described in Scheme II for synthesizing formula (c) compounds. Hydrogenation of formula (p) compounds dissolved in a suitable organic solvent such as ethyl acetate and hexane using an appropriate hydrogenation agent such as platinum dioxide, Raney nickel, or palladium on carbon (Pd/carbon) yields formula (q) compounds. Hydrolysis of the alkyl phosphinate ester with a base such as sodium hydroxide, potassium hydroxide, lithium hydroxide, or potassium carbonate dissolved in an aqueous $C_{1-6}$alkyl alcohol solution, such as methanol, yields a salt of a formula (s) compound. Treatment of the salt with strong acid yields a formula (s) compound. Hydrolysis may also be carried out using trimethylsilyl iodide in acetonitrile to give formula(s) compounds.

Formula (s) compounds in which X is other than hydrogen or fluoro are prepared using processes such as exemplified in Examples 23, 24 and 25.

SCHEME IV

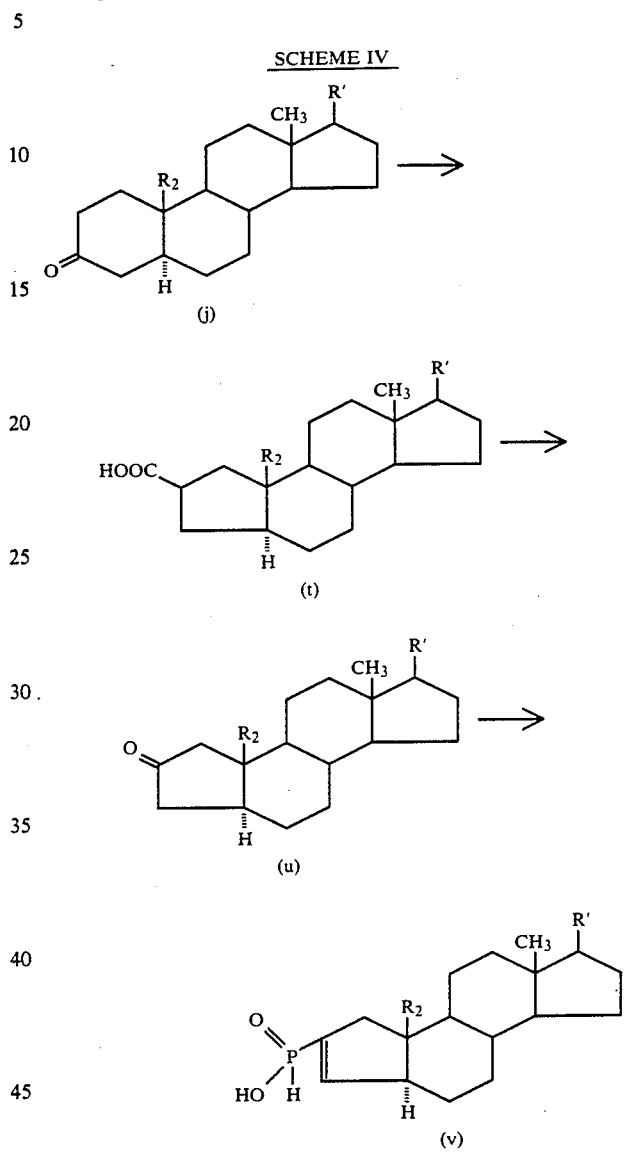

Scheme IV depicts formation of Formula (I) compounds in which n is 0. The starting materials for this formation are formula (j) compounds prepared as described in Scheme III. According to Scheme IV, formula (j) compounds are dispersed in a strong acid, preferably glacial acetic acid, and treated with thallic acetate sesquihydrate to prepare A-nor-2-carboxylic acid formula (t) compounds. Formula (u) compounds next are prepared from formula (t) compounds by treating with lithium diisopropylamide, dimethyl sulfide, the N-chlorosuccinimide and sodium bicarbonate, followed by hydrochloric acid.

Formula (u) compounds are then converted to the phosphinic acids by treating the trifluoromethylsulfonate with tetrakis(triphenylphosphine)palladium(0) and hypophosphorous acid.

SCHEME V

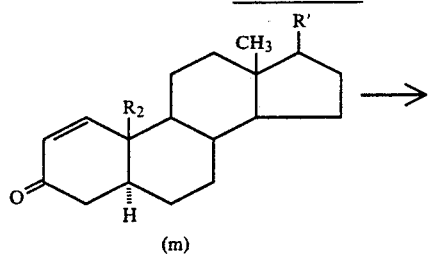
(m)

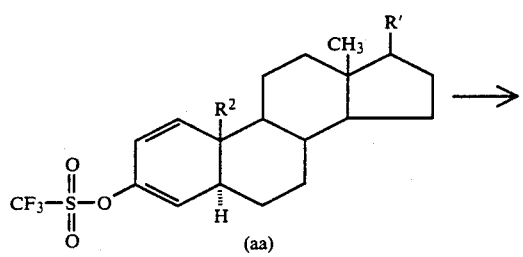
(aa)

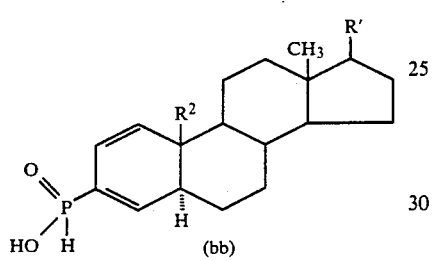
(bb)

Scheme V outlines formation of Formula (I) compounds containing the 1,3-diene moiety. The starting materials in Scheme V are formula (m) compounds prepared as described in Scheme III. According to Scheme V, formula (aa) compounds are prepared from formula (m) compounds by procedures described in Scheme III. Compounds of formula (aa) are treated with tetrakis(triphenylphosphine)palladium (0), or a similar catalyst and an organic base, such as triethylamine, in a suitable solvent, such as dimethylformamide, with hypophosphorous acid to give the phosphinic acid compounds of formula (bb).

SCHEME VI

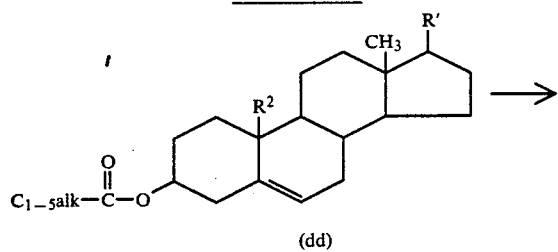
(dd)

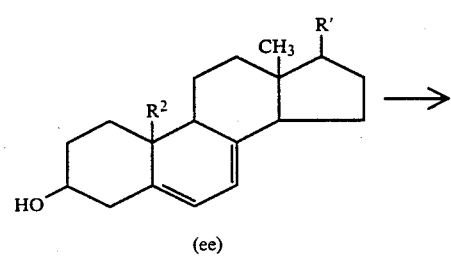
(ee)

-continued
SCHEME VI

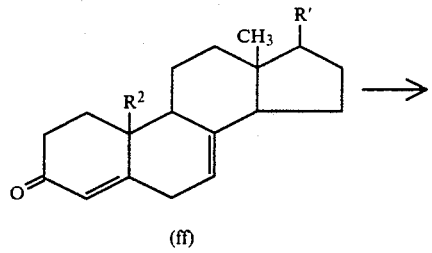
(ff)

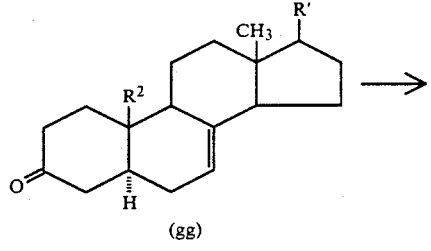
(gg)

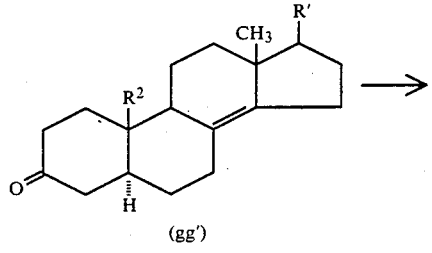
(gg')

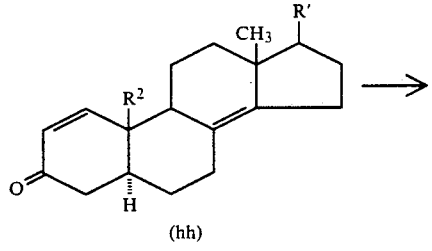
(hh)

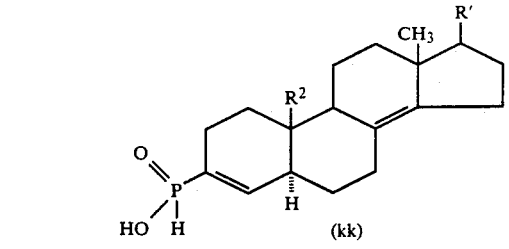
(kk)

Scheme VI shows synthesis of phosphonic acid compounds and alkyl esters thereof in which there is a $C_8$–$C_{14}$ double bond. The formula (dd) starting materials are known and available and can be synthesized from available materials using known methods. Formula (ee) compounds are prepared by first treating formula (dd) compounds in a suitable organic solvent such as hexane with a brominating agent such as N-bromosuccinamide or dibromantin and a mild base such as sodium bicarbonate, and heated. Thereafter, the mixture is treated with lithium bromide (LiBr), cooled to −20° C. to 20° C., preferably 0° C., and treated with triethylamine and benzenethiol. Treatment with an oxidizing agent such as sodium periodate, hydrogen peroxide, or m chloroperbenzoic acid and is followed by heating to 40° C. to 100° C., preferably 70° C., and treatment with an organic base such as trimethylamine, or preferably triethylamine. Treatment with a strong base such as sodium hydroxide, potassium hydroxide, lithium hydroxide, or potassium carbonate yields formula (ee) compounds.

Formula (ee) compounds then are dissolved in a suitable organic solvent such as toluene, and treated with an alkyl ketone agent such as a cyclohexanone, or butanone followed by treatment with aluminum isopropoxide and heating to prepare formula (ff) compounds. Reaction of formula (ff) compounds as described in forming Scheme III, formula (j) compounds yields formula (gg) compounds. Hydrogenation of formula (gg) compounds using suitable catalysts such as platinium dioxide, Raney nickel, or Pd/carbon, yields formula (gg') compounds. Formula (hh) compounds then are prepared by adding phenylselenyl chloride to a formula (gg') compound dissolved in a suitable organic solvent, preferably ethyl acetate, followed by addition of an oxidizing agent such as $H_2O_2$. Substitution of formula (hh) compounds for formula (m) compounds in Scheme III yields the alkyl ester of the 1,3,8(14)-triene-3-phosphinic acid compound, which is hydrogenated to give the 3,8(14)-diene-phosphinic acid ester, which is hydrolized to give the 3,8(14)-diene phosphinic acid compound of formula (kk).

SCHEME VII

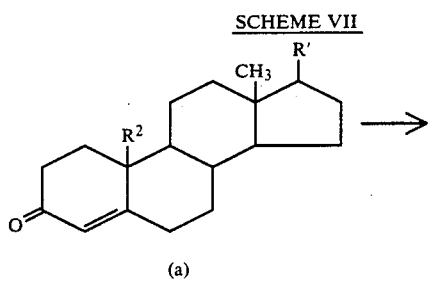
(a)

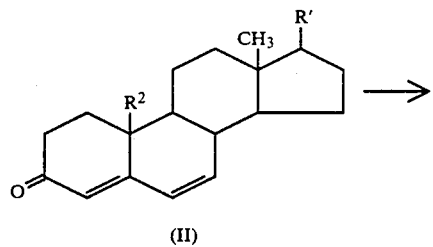
(ll)

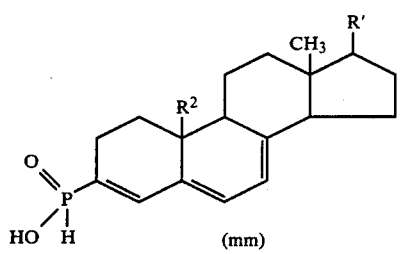
(mm)

Scheme VII outlines formation of Formula (I) compounds having $C_{3-4}$, $C_{5-6}$ and $C_{7-8}$ double bonds. Treatment of formula (a) compounds in a suitable solvent such as t butanol with chloranil, with heating up to reflux temperatures, yields formula (ll) compounds. Thereafter, substituting formula (ll) compounds for formula (a) compounds in the Scheme II process yields alkyl phosphinates and phosphinic acid compounds of formula (mm).

SCHEME VIII

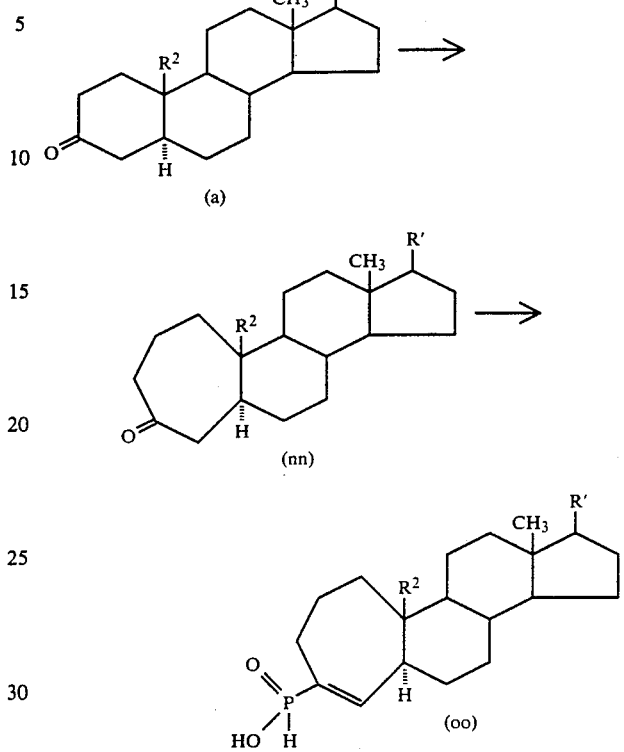

Scheme VIII shows formation of Formula (I) compounds in which n is 2 from Scheme I, formula (a) compounds. Formula (nn) compounds are prepared by treatment of formula (a) compounds in a suitable organic solvent such as diethyl ether and methanol cooled to $-20°$ C. to $20°$ C., preferably $0°$ C., with a strong base such as sodium hydroxide, lithium hydroxide, potassium carbonate, or potassium hydroxide (KOH), followed by treatment with a diazomethane precursor such as N-methyl-N'-nitro N-nitrosoguanidine or N-methylnitrosourea. Substituting formula (nn) compounds for formula (a) compounds in the process of Scheme I yields formula (oo) compounds.

SCHEME IX

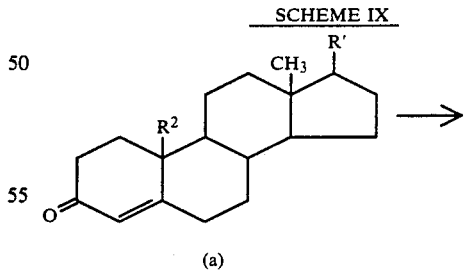
(a)

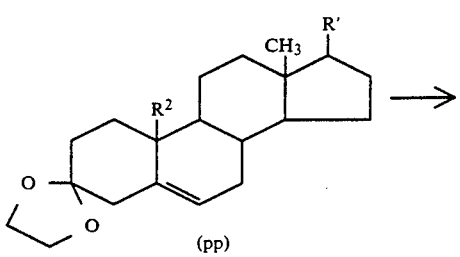
(pp)

-continued
SCHEME IX

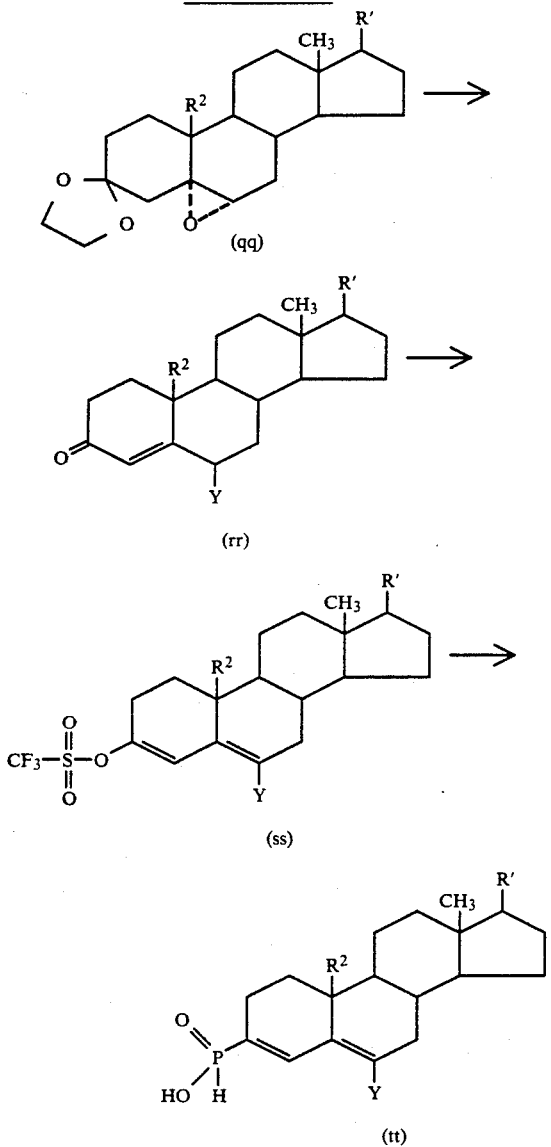

Scheme IX outlines formation of Formula (I) compounds in which Y is chloro or fluoro from Scheme I, formula (a) compounds. Formula (pp) compounds are prepared by reacting formula (a) compounds with a suitable keto group protecting agent such as ethylene glycol in the presence of an acid catalyst such as p-toluene sulfonic acid. Treatment of formula (pp) compounds with a suitable oxidizing agent such as m chloroperbenzoic acid in a suitable organic solvent such as dichloromethane yields formula (qq) epoxide compounds.

Formula (rr) compounds then are prepared by adding gaseous hydrogen fluoride or hydrogen chloride to a formula (qq) compound in a suitable organic solvent such as chloroform, or (where Y=F) by adding borontrifluoride etherate to a formula (qq) compound in a suitable organic solvent such as benzene:ether followed by treatment with strong acid such as hydrogen chloride in glacial acetic acid. Next, 2,6 di-t-butyl-4-methylpyridine followed by trifluoromethanesulfonic anhydride are added to a formula (rr) compound to yield a formula (ss) compound. Reaction of a formula (ss) compound by the procedure of Scheme II gives formula (tt) ph-osphinic acid compounds of this invention. Compounds of Formula (i) in which Y is trifluoromethyl are prepared by processes such as exemplified in Example 24.

Compounds having double bond at $C_{11}$ are prepared by modifications of the Schemes I through IX by procedures which would be apparent to those skilled in the art and are exemplified in Example 33, below.

The 3,5,11-triene compounds of Formula I are prepared from 11-oxo compounds by reaction in an appropriate solvent such as methylene chloride with a base such as 2,6-di-t-butyl-4-methylpyridine and a trihaloalkyl sulfonic anhydride such as trifluoromethane sulfonic anhydride to give an 11-ene-11-trifluorosulfonate (enoltriflate) compound. The triflate group is reduced to provie the 3,5,11-triene compounds.

The 2-ene compounds of Formula I are prepared by converting 5α-3-oxo-compounds to 5=-2-ene-3-triflates in an appropriate solvent such as tetrahydrofuran with lithium bis(trimethylsilyl)amide and a sulfonating agent such as N-phenyltrifluoromethanesulfonimide at a reduced temperature of about $-100°$ to $20°$ C. The triflate compounds are converted to phosphinic acid and alkyl esters of alkylphosphinic acid compounds by procedures of Schemes II and III followed by hydrolysis of the phosphinate ester groups with, for example, trimethylsilyl iodide to provide 3 alkyl-phosphinic acid compounds. Catalytic hydrogenation of the 2-ene compounds of Formula I provide the A ring saturated compounds of Formula I.

In the above Schemes, the starting materials are selectd so that the $R^2$ and $R^1$ groups in the formula (a) compound are the same as the $R^2$ and $R^3$ groups in the Formula (I) compound being synthesized. Alternatively, the $R^2$ and $R^1$ groups of the formula (a) compound are selected so that they can be converted by known procedures to the $R^2$ and $R^3$ groups of the target Formula (I) compounds by additional steps in the synthetic process. For example, Formula (I) compounds wherein $R^3$ is carboxylic acid are converted to the corresponding amides by reaction with amines or substituted amines via the corresponding acid chlorides. Similarly, Formula (I) compounds wherein $R^3$ is $CH_3CHCOOH$ are prepared by oxidation of the corresponding alcohol.

Pharmaceutically acceptable acid addition salts of the compounds of the invention containing a basic group are formed where appropriate with strong or moderately strong organic or inorganic acids in the presence of a basic amine by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

Because Formula (I) compounds inhibit steroid 5α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy, and male pattern baldness. several compounds of the invention were tested for potency in inhibiting human steroid 5α-reductase using tissue from hyperplastic human prostates. In determining potency in inhibiting the human enzyme, the following procedure was employed:

Frozen human prostates were thawed and minced into small pieces (5 mm³). The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier (Branson Sonic Power Co.) followed by hand homogenization in a glass-to-glass Dounce homogenizer (Kontes Glass Company, Vineland, N.J.).

Prostatic particles were obtained by differential centrifugation at 600 to 1000 × g for 20 minutes and 140,000 × g for 60 minutes at 4° C. The pellet obtained from the 140,000 × g centrifugation was washed with 5 to 10 tissue volumes of the buffer described above and recentrifuged at 140,000 × g. The resulting pellet was suspended in 20 mM potassium phosphate buffer, pH 6 5, containing 20% glycerol, 1 mM dithiothreitol, and 50 μM NADPH. The suspended particulate solution was stored at −80° C.

A constant amount of $[^{14}C]$-testosterone (52 to 55 mCi/mmol, New England Nuclear, Boston, Mass.) in ethanol and varying amounts of the potential inhibitor in ethanol were deposited in test tubes and concentrated to dryness in a SAVANT Speed Vac. To each tube was added buffer, 20 μl of 10 mM NADPH and an aliquot of prostatic particulate solution to a final volume of 1.0 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androst-aneidiol, and androst-anedione as carriers. The organic layer was removed to a second test tube and evaporated to dryness in a Speed Vac. The residue was dissolved in 20 to 30 μl chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant (Ki) can be calculated from equation 1:

$$K_i = (B/A)/(S/K_m + 1)$$  Equation 1 where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 μM.

Table II displays the results of the above testing and shows that the tested compounds of the invention are potent inhibitors of human steroid 5α-reductase.

TABLE II

| Inhibition Constants of Human Prostatic Steroid 5α-Reductase | |
|---|---|
| Compound | $K_i$, app (nM) |
| Example 5 | 25 |
| Example 1 | 7 |
| Example 2 | 35 |
| Example 3 | 15 |
| Example 7 | 20 |
| Example 9 | 55 |

In vivo activity in inhibiting steroid 5α-reductase activity may be demonstrated by the following procedure. Male Charles River CD rats, 48 days old, weighing approximately 200 gm are administered 10 mg/kg of the compound to be tested dissolved in propylene glycol and diluted in normal saline. Following compound administration the animals are sacrificed, the ventral prostates are excised, and DHT levels are measured by the following procedure.

Prostate tissue is excised, trimmed, weighed, minced and washed with phosphate buffer. The tissue then is homogenized in Phosphate buffer and extracted by addition of ethyl acetate and mixing on an orbital mixer for forty-five minutes. The ethyl acetate is evaporated, the residue is reconstituted in ethanol, and was centrifuge filtered using 0.45 μM filter paper. The components then are separated using reverse-phase HPLC collecting the DHT fraction. The fraction is reduced to dryness and reconstituted in standard DHT assay buffer available from Amersham. DHT levels then are measured using standard techniques such as radioimmunoassay.

The compounds of Formula (I) are incorporated into convenient dosage forms such as capsules, tablets, or injectable preparations. Solid or liquid pharmaceutical carriers are employed. Solid carriers include, starch, lactose, calcium sulfate dihYdrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.001–100 mg/kg of active compound, preferably 0.01–10 mg/kg. The selected dose is administered to a human patient in need of steroid 5α-reductase inhibition from 1-6 times daily, topically, orally, rectally, by injection, or continuously by infusion or less often than once a day depending on the pharmacokinetics of the compound. Oral dosage units for human administration preferably contain from 1 to 500 mg of active compound. Parenteral administration uses lower dosages. Oral administration is preferred and convenient for the patient.

The method of this invention of inhibiting steroid 5α-reductase activity in mammals, including humans, comprises administering to a subject in need of such inhibition an effective steroid 5α-reductase inhibiting amount of a compound of Formula (I).

The following examples illustrate preparation or compounds and pharmaceutical compositions of this invention. The examples are not intended to limit the scope of the invention as defined and claimed herein.

EXAMPLE 1

17β-N,N-Diisopropylcarboxamido-androst-3,5-diene-3-phosphinic acid (i) Androst-4-ene-3-one-17β-carboxylic acid Methyl androst-4-ene-3-one-17B-carboxylate (20 g, 60 mmol) was dissolved in 700 ml of a 20:1 solution of methanol:water and potassium hydroxide (7 g) was added and the solution was refluxed under argon for 24 hours. The reaction mixture was then acidified with 5% hydrochloric acid and 250 ml water was added. After aging for 1 hour, the mixture was filtered and dried to yield 18 g (94%) of androst-4-ene-3-one-17β-carboxylic acid as a white crystalline solid.

(ii) Androst-4-ene-3-one-17β-N,N-diisooropylcarboxamide

A solution of androst-4-ene-3-one-17β-carboxylic acid (18 g, 0.06 mol) in 350 ml of toluene was azeotropically dried until approximately 100 ml distillate was collected. The solution was then cooled to 10° C. Pyridine (6.7 ml, 0.08 mol) was added, followed by slow addition of a solution of oxalyl chloride (7.2 ml, 0.08 mol) in 10 ml of toluene. The reaction mixture was stirred at room temperature (under argon) for 2 hours, and then cooled to 0° C. A solution of diisopropylamine (89 ml, 0.6 mol) in 40 ml toluene was added dropwise such that the temperature did not exceed 40° C. The reaction mixture was stirred for 1 hour and then quenched with 300 ml ice water. The layers were separated and the aqueous layer was extracted 4 times with ethyl acetate (800 ml). The organic layers were combined and washed with 5% hydrochloric acid and brine. The organic layer was then dried over sodium sulfate and concentrated to dryness. Recrystallization by dissolving in 10 ml toluene and adding 200 ml hexane afforded 16.5 g (69%) of androst-4-ene-3-one-17β-N,N-diisopropylcarboxamide (m.p. 236°–239° C.). (iii) 17β-N,N-Diisopropylcarboxamido-androst-3,5-diene-3-phosphinic acid To a solution of 1 g (2.5 mmole) of 17β-N,N-diisopropylcarboxamido-3-oxo-androst-4-ene in 25 ml of THF was added 1 g of 95% hypophosphorous acid, and the reaction was stirred at 65° C. under argon for 48 hours. The solvent was removed under vacuum, the residue was dissolved in methylene chloride and the organic layer was washed several times with water to neutrality. The dried, concentrated crude product was crystallized from methanol/water to afford 1.07 g of the white, crystalline 17β-N,N-diisopropylcarboxamide-androst-3,5-diene-3-phosphinic acid; m.p. 134°–140° C.

EXAMPLE 2

17β-N-t-Butylcarboxamide-androst-3,5-diene-3-phosphinic acid

The preparation of the title compound was analogous to Example 1 using t-butylamine in place of diisopropylamine. The title compound was crystallized from methanol/water; m.p. 230° C. (dec).

EXAMPLE 3

17β-N,N-Diisopropylcarboxamide-5α-androst-2-ene-3-phosphinic Acid (i) 3-Oxo-5α-androstane-17β-N,N-diisopropyl carboxamide Ammonia (500 mL) was double distilled into a flask equipped with a dry ice condenser and an argon bubbler. Lithium (1 g) was dissolved in the ammonia. Freshly distilled aniline (185 g) was added followed by a solution of 17β-N,N-diisopropylcarboxamido-3-oxo-androst-4-ene (10 g) in dry THF (200 mL) that was added dropwise. Then the reaction was stirred at −78° C. to −33° C. for 2 hours, and then quenched with isoprene until the blue color was discharged. The ammonia was allowed to evaporate and the residue was then diluted with aqueous ammonium chloride and extracted with ethyl acetate. Chromatography on silica gel (10% ethyl acetate in hexanes) of the concentrated organic extract yielded the title compound.

(ii) 17β-N,N-diisopropylcarboxamido03-(trifluoromethylsulfonate)-5α-androst-2-ene A solution of lithium bis(trimethylsilyl)amide (4.4 mmol, 2.2 eq) in 2 ml THF was cooled to −78° C. A solution of 3-oxo-5α-androstane 17β-N,N-diisopropylcarboxamide (20 mmol) in 10 ml THF was added and the reaction mixture was stirred for 1 hour. A solution of N-phenyltrifluoromethanesulfonimide (857 mg, 2.4 mmol) in 8 ml THF was then added and the reaction mixture was stirred for 1.5 hours at −78° C. The reaction mixture was then evaporated to dryness and chromatographed on silica gel eluting with 20% ethyl acetate in hexane. Trituration in a hexane and ether solution afforded the desired product, 17β-(N,N-diisopropylcarboxamide)-3-(trifluoromethylsulfonate)-5α-androst-2-ene.

(iii) 17βN,N-Diisopropylcarboxamido-5α-androst-2ene-3-phosphinic acid

To a solution of 200 mg (0.375 mmole) of 17β-N,N-diisopropyl-carboxamido-3-trifluoromethylsulfonate-5α-androst-2-ene in 40 ml of DMF were added 0.24 mL (4.6 eq.) of triethylamine, 50 mg of tetrakis (triphenylphosphine) palladium (0) and 300 mg (excess) of hypophosphorous acid. The reaction was stirred under argon for 3 hours and poured into water. The product was extracted into methylene chloride and the organic layer was washed with water (3×), dilute HCl (1×), saturated NaHCO$_3$ and brine. The dried, concentrated product had an Rf of 0.11 on silica gel with a system of CHCl$_3$/MeOH/H$_2$O at 80:20:2 that stained blue with a molybdenum spray reagent. Chromatography over silica gel with this system gave a white solid which was crystallized from acetonitrile (charcoal) to give 17β-N,N-diisopropyl-carboxamido-5α-androst-2-ene-3-phosphinic acid; m.p. 20°–225° C.

EXAMPLE 4

17β-N-t-Butylcarboxamido-5α-androst-2-ene-3-phosphinic acid

The title compound is prepared according to Example 3 by using 17β-N-t-butylcarboxamido-3-oxoandrost-4-ene in place of 17β-N,N-diisopropylcarboxamido-3-oxo-androst-4-ene.

EXAMPLE 5

17β-N,N-Diisopropylcarboxamido-5α-androst-3-ene-3-phosphinic acid (i)

17β-N,N-Diisopropylcarboxamido-3-trifluoromethyl-sulfonate-5α-3-ene

Ammonia (500 mL) was double distilled into a flask equipped with a dry ice condenser and an argon bubbler. Lithium (1 g) was dissolved in the ammonia. Freshly distilled aniline (185 g) was added followed by a solution of 17β-N,N-diisopropylcarboxamido-3-oxo-androst-4-ene (10 g) in dry THF (200 mL) that was added dropwise. The reaction was stirred at −78° C. to −33° C. for 2 hours, and then quenched with isoprene until the blue color was discharged. The volatiles were slowly evaporated and then the residue was pumped at 0.5 mmHg for 1 hour. The oily residue was dissolved in dry THF (200 mL), cooled to 0° C. and a solution of N-phenyltrifluoromethylsulfonimide (25 g) in THF (100 mL) was added. This mixture was stirred at 0° C. for 18 hours, concentrated to dryness and the residue was chromatographed on silica gel with 10% ethyl acetate in hexane to afford 17β-N,N-diisopropylcarbox-amido-3-trifluoromethylsulfonate-5α-androst-3-ene (8.6 g, 64%).

(ii)

17β-N,N-Diisopropylcarboxamido-5α-androst-3-ene-3-phosphinic acid

The title compound was prepared according to Example 3 by using 17β-N,N-diisopropylcarboxamido-3-trifluoromethylsulfonate-5α-androst-3-ene in place of 17β-N,N-diisopropylcarboxamido-3-trifluoro-methyl-sulfonate-5α-androst-2-ene. The title compound was a white solid, m.p. 228°–232° C.

EXAMPLE 6

17β-N,N-butylcarboxamido-5α-androst-3-ene-3-phosphinic acid

The title compound is prepared according to Example 5 by using 17β-N-t-butylcarboxamido-3-oxo-androst-4-ene in place of 17β-N,N-diisopropylcarbox-amido-3-oxo-androst-4-ene.

EXAMPLE 7

7β-N,N-Diisopropylcarboxamido-androst-2,4-diene-3-phosphinic acid

The title compound was prepared according to Example 3 (ii-iii) by using 17β-N,N-diisopropylcarbox-amido-3-oxo-androst-4-ene in place of 17β-N,N-diiso-propyl-carboxamido-3-oxo-5α-androstane.

EXAMPLE 8

17β-N-t-Butylcarboxamido-androst-2,4-diene-3-phosphinic acid

The title compound is prepared by the method described in Example 7 by using 17β-N-t-butylcarboxa-mido-3-trifluoromethylsulfonate-androst-2,4-diene in place of 17β-N,N-diisopropylcarboxamido-3-trifluoro-methylsulfonate-androst-2,4-diene.

EXAMPLE 9

17β-N,N-diisopropylcarboxamido-androst-3,5-diene-3-methylphosphinic acid (i)

17β-(N,N-Diisopropylcarboxamide)-3-(trifluoromethylsulfonate)-androst-3,5-diene

Androst-4-ene-3-one-17β-N,N-diisopropylcarboxa-mide (5 g, 12.5 mmol) was dissolved into 50 ml of methylene chloride. 2,6-Di-t-butyl-4-methylpyridine (3.08 g, 17.0 mmol) was then added to the steroid solution and stirred at room temperatre for 15 minutes. Trifluorome-thanesulfonic anhydride (3.5 ml, 19 mmol) was added to the solution and stirring continued for 30 minutes. The reaction mixture was then diluted with 50 ml methylene chloride and filtered. The organic layer was washed twice with 5% hydrochloric acid, saturated sodium bicarbonate, and brine. It was then dried over sodium sulfate and evaporated. The triflate was purified by chromatography on silica gel eluting with 20% ethyl acetate in hexane to yield 4 g (61%) of 17β-(N,N-diiso-propylcarboxamide)-3-(trifluoromethylsulfonate)-androst-3,5-diene.

(ii)

17β-N,N-diisopropylcarboxamido-androst-3,5-diene-3-methylphosphinic acid methyl ester A solution of 17β-N,N-diisopropylcarboxamido-3-trifluoromethylsulfonate-androst-3,5-diene (400 mg, 0.75 mmole) in 10 ml of DMF was treated according to Example 3(iii) but using methylphosphinic acid methyl ester (80 μL) in place of hypophosphorus acid and proportional quantities of other reagents to provide after chromatography on silica gel with an ethyl acetate/hexane gradient the title compound as a white solid.

(iii)

17β-N,N-diisopropylcarboxamido-androst-3,5-diene-3-methylphosphinic acid

In 5 mL of acetonitrile was dissolved 250 mg (0.5 mmole) of methyl (17β-N,N-diisopropylcarboxamido-androst-3,5-diene-3)-phosphinic acid methyl ester. The solution was flushed with argon and 150 mg (1 mmole) of sodium iodide and 0.13 mL (1 mmole) of trimethyl-silyl chloride was added. The reaction mixture was stirred at room temperature under argon for 24 hours, diluted with chloroform and the organic layer was washed with water, dilute HCl, brine and sodium sulfite solution. The dried concentrated product was purified by HPLC on a reverse phase C-18 column eluting with 70% methanol and 30% of 20 mmole phosphate buffer (pH 6.6) to afford the title compound as its potassium salt.

EXAMPLE 10

20α-(Hydroxymethyl)5α-pregn-3-ene-3-phosphinic acid

(i) 20α-(Hydroxymethyl)-pregn-4-ene-3-one

Pregn-4-ene-3-one-20%-carboxaldehyde (16.4 g, 50 mmol) in ethanol (250 ml) and THF (50 ml) was cooled in 0° C. and a solution of sodium borohydride (NaBH$_4$) in 125 ml ethanol was added dropwise. The reaction mixture was stirred overnight at 25° C. Acetic acid was added to the reaction mixture until neutral pH and then the solution was evaporated to remove excess ethanol. The residue was dissolved in trichloromethane and washed with saturated sodium bicarbonate solution, water and brine. The organic layer was then dried over sodium sulfate and evaporated to dryness to yield 13.9 (82%) of 20α-(hydroxymethyl)-pregn-4-ene-3-one.

(ii) 20α-(t-Butyldimethylsilyloxymethyl)-pregn-4-ene-3-one

A solution of 20α(hydroxymethyl)-pregn-4-ene-3-one (1.2 g, 3.5 mmol), t-butyldimethylsilyl chloride (627 mg, 4.15 mmol) and imidazole (287 mg, 4.22 mmol) in DMF (40 ml) was stirred overnight at 40° C. The reaction mixture was then poured onto ice water and the emulsion was washed three tmes with ethyl acetate. The organic layers were combined, washed with cold dilute hydrochloric acid, water and brine; dried over sodium sulfate and evaporated to dryness. Recrystallization from methanol afforded 1.1 g (70%) of 20α-(t-butyldimethylsilyloxymethyl)pregn-4-ene-3-one.

(iii) 20α-(t-Butyldimethylsiloxymethyl)-3-trifluoromethylsulfonate)-5α-pregn-3-ene Ammonia (200 ml) was double distilled into a 3-neck roundbottom flask equipped with a dry ice condenser and argon bubbler. Ltihium (wire (120 mg, 17.4 mmol) was dissolved in ammonia (NH$_3$). A solution of 20α-(t-butyldimethylsiloxymethyl)-pregn-4-ene-3-one (3 g, 6.76 mmol) and aniline (49.5, 1, 5.4 mmol) in THF (50 ml) was added dropwise to the Li/NH$_3$ solution. The reaction mixture was stirred at −78° C. for 15 mionutes and then quenched with isoprene until the blue color disappeared. The volatiles were slowly evaporated (to avoid excess foaming) by slow warming, and eventually at 0.5 mmHg for 1 and ½ hours. The residue was redissolved in THF (50 ml) and cooled to 0° C. A solution of N-phenyltrifluoromethylsulfonimide (7 g, 20 mmol) in THF (10 ml) was added to the reaction mixture, and stirring was continued overnight at 4° C. The solvent was then evaporated and the residue was chromatographed on silica gel eluting with 3% ethyl acetate in hexane to yield 2.24 g (57%) of the 20α-(t-bu8tyldimethylsiloxymethyl)-3-(trifluoromethylsulfonate)-5α-pregn-3-ene.

(iv) 2060-(t-Butyldimethylsiloxymethyl)-3-(trifluoromethylsulfonate)-5α-pregn-3-ene-3-phosphinic acid 20α-(t-Butyldimethylsiloxymethyl)-3-(trifluoromethylsulfonate)-5α-pregn-3-ene (100 mg, 0.174 mmol) is dissolved and DMF (1 ml). Triethylamine (55 μl, 0.3866 mmol), triphenylphosphine (9 mg, 0.034 mmol) and palladium(II) acetate (3.8 g, 0.017 mmol), and 150 mg of 95% hypophosphorus acid are added. The reaction mixture is then stirred overnight at 45° C. under argon, diluted with ethyl acetate and washed with water The organic layer is dried over sodium sulfate and evaporated. The oil is purified by chromatography to yield 20α-(t-butyldimethylsiloxymethyl)-5α-pregn-3-ene-3-phosphinic acid.

(v) 20α-(Hydroxymethyl)-5α-pregn-3-ene-3-phosphinic acid

20α-(t-butyldimethylsiloxymethyl)-5α-pregn-3-ene-3-phosphinic acid (500 mg), is dissolved in THF (20 ml) and 2 ml of a 1 molar solution of tétrabutylammonium fluoride in THF is added. The reaction mixture is stirred at room temperature for 3.5 hours and then diluted with water. The aqueous mixture is washed thoroughly with dichloromethane. The organic layers are combined, dried over sodium sulfate and evaporated to dryness Purification by chromatography affords 20α-hydroxymethyl-5α-pregn-3-ene-3-phosphinic acid.

EXAMPLE 11

17β-(N,N-Diisopropylcarboxamide)-4-fluoro-5α-androst-3-ene-phosphinic Acid

(i) 3Oxo-5α-androst-1-ene-17β-N,N-diisopropylcarboxamide

To a solution of 3-oxo-5α-androstane-17β-N,N-diisopropylcarboxamide (2.3 g, 5.74 mmol) in 100 ml ethyl acetate was added phenylselenylchloride (1.1 g, 5.74 mmol) and the reaction mixture was stirred for 2 hours. The reaction mixture was then washed with 5% sodium bicarbonate solution and brine. The ethyl acetate solution was cooled to 0° C. and 50 ml THF was added. Hydrogen peroxide (6 ml of a 30% solution) was slowly added and the reaction mixture stirred for 2 hours. The reaction mixture was then washed with 5% sodium bicarbonate solution, brine and evaporated to dryness Purification by chromatography on silica gel eluting with 20% ethyl acetate in hexane afforded 1.3 g 3-oxo-5α-androst-1-ene-17β-N,N-diisopropylcarboxamide.

(ii) 3-Oxo-5α-androstane-1,2-alpha-epoxide-17β-N,N-diisopropylcarboxamide

3-Oxo-5α-androst-1-ene-17β-N,N-diisopropylcarboxamide (4.6 g, 11.5 mmol) was dissolved in 50 ml methanol and cooled to 15° C. To the solution was added hydrogen peroxide (0.8 ml of a 30% solution) followed by sodium hydroxide (0.16 ml of a 10% solution) in 2 ml methanol. The ice bath was removed and stirring was continued at room temperature for 1 hour. The reaction mixture was then poured into ice water and washed twice with dichloromethane. The organic layers were combined and washed with water and brine; dried over sodium sulfate and evaporated. Trituration in acetone afforded 4.0 g (83.7%) of the desired epoxide; 3-oxo-5α-androstane-1,2α-epoxide-17β-N,N-diisopropylcarboxamide.

(iii) 3-Oxo-4-fluoro-5α-androst-1-ene-17β-N,N,diisopropylcarboxamide

3-Oxo-5α-androstane-1,2%-epoxide-17β-N,N-diisopropylcarboxamide (1.7 g, 4 mmol) was dissolved in 25 ml THF and cooled to −20° C. Pyridinium poly(hydrogen fluoride) (10 ml) was slowly added to the solution (under argon). The reaction mixture was warmed to 0° C., stirred 30 minutes then warmed to room temperature and stirred for 15 minutes. The reaction mixture was poured into ice water and washed with ethyl acetate. The organic layer was washed with water, 5% sodium bicarbonate solution and brine; dried over sodium sulfate and evaporated. Purification by chromatography on silica gel eluting with 20% ethyl acetate in hexane yielded 750 mg (44%) of the desired 3-oxo-4-fluoro-5α-androst-1-ene-17β-N,N-diisopropylcarboxamide.

(iv)
17β-(N,N-Diisopropylcarboxamide)-3-(trifluoromethylsulfonate)-4-fluoro-5α-androst-1,3-diene A solution of lithium bis(trimethylsilyl)amide (4.2 mmol, 2.2 eq) in 2 ml THF was cooled to −78° C. A solution of 3-oxo-4-fluoro-5α-androst-1-ene-17β-N,N-diisopropylcarboxamide (800 mg, 1.9 mmol) in 10 ml THF was added and the reaction mixture was stirred for 1 hour. A solution of N-phenyltrifluoromethanesulfonimide (857 mg, 2.4 mmol) in 8 ml THF was then added and the reaction mixture was stirred for 1.5 hours at −78° C. The reaction mixture was then evaporated to dryness and chromatographed on silica gel eluting with 20% ethyl acetate in hexane. Trituration in a hexane and ether solution afforded 460 mg (46%) of the desired product, 17β-(N,N-diisopropylcarboxamide)-3-(trifluoromethylsulfonate)-4-fluoro-5α-androst-1,3-diene.

(v)
17β-N,N-Diisopropylcarboxamide-4-fluoro-5α-androst-1,3-diene-3-phosphinic acid The title compound is prepared according to Example 3 (iii) by substituting 17β-(N,N-diisopropylcarboxo amide-3-(trifluoromethylsulfonate)-4-fluoro-5α-1,3-diene for 17β-N,N-diisopropylcarboxamido-3-(trifluoromethyl-sulfonate)-5α-androst-2-ene.

(vi)
17β-N,N-diisopropylcarboxamido-4-fluoro-5α-androst-3-ene-3-phosphinic acid

17β-N,N-diisopropylcarboxamido-4-fluoro-5α-androst-1,3-diene phosphinic (150 mg) in 20 mL of a 3:1 solution of ethyl acetate and hexane is hydrogenated at 25° C. and 1 atmosphere over 30 mg of 10% of palladium on carbon. The suspension was filtered and concentrated to a white solid (150 mg). Trituration with methanol/acetone o provides 17β-N,N-diisopropylcarboxamido-4-fluoro-5α-androst-3-ene-3-phosphinic acid.

EXAMPLE 12

17β-(N,N-Diisopropylcarboxamide)-A-nor-5α-androst-2-ene-2-phosphinic acid (i) 17β-(N,N-Diisopropylcarboxamide)-A-nor-5α-androstane-2-carboxylic acid)

A solution of 17β-(N,N-diisopropylcarboxamide)-3-oxo-5α-androstane (1 g) in 95% acetic acid (25 ml) is treated with thallium acetate sesquihydrate (3.85 g), and the mixture is heated in an oil bath held at 80° C. for 2 hours under argon according to the procedure in Tetrahedron, %8, 5337–5339 (1972). The mixture is cooled, diluted with ice water and extracted with ethyl acetate. The organic extracts are washed to neutrality, dried and concentrated to the crude product. A precipitation from methanol-acetone-ethyl ether gives 17β-(N,N-diisopropyl-carboxamide)-A-nor-5α-androstane-2-carboxylic acid.

(ii)
17β-(N,N-Diisopropylcarboxamide)-A-nor-3-oxo-5α-androstane

A solution of 17β-(N,N-diisopropylcarboxamide)-A-nor-5α-androstane-2-carboylic acid (432 mg, 1 mmol) in 15 mL of dry THF and 2 mL of HMPA is added at −20° C. to lithium diisopropylamide (2.2 mmol) in 10 ml of THF. The mixture is stirred at −20° C. for 1 hour and at 0° C. for 1 hour. Then dimethyl disulfide (1.5 mmol) is added (according to the procedure of *J. Amer. Chem. Soc.* 99, 3101 (1977)) at 0° C. After 30 minutes the reaction is quenched with ice water and washed with 2N aqueous sodium bicarbonate solution and these water washings are combined with the original water layer, cooled and acidified with Hcl. The product is extracted into ethyl acetate, dried and concentrated to the sulfenylated acid. This crude product is dissolved in absolute ethanol (5 mL) anhydrous sodium bicarbonate (1.5 mmol) is added. Then solid Nchlorosuccinimide (2.3 mmol) is added portionwise and the reaction mixture is stirred for 2 hours at 25° C. A few drops of saturated aqueous sodium sulfite are added and this is followed by 2 mL of 1N HCl. After being stirred for 30 minutes, the reaction is diluted with water, extracted with ethyl acetate and washed with dilute NaHC03 solution. The dried, concentrated product affords 17β-(N,N-diisopropylcarboxamide)-A-nor-2-oxo-5α-androstan eafter precipitation from acetone-hexane-ethyl ether.

(iii)
17β-(N,N-Diisopropylcarboxamide)-2-trifluoromethylsulfonate-A-nor-5α-androst-2-ene 17β-N,N-Diisopropylcarboxamide-A-nor-2-oxo-5α-androstane is converted to the enol triflate by the method described in Example 3(ii) using lithium bis(-trimethylsilyl)amide and phenyltrifluoromethylsulfonimide.

(iv)
17β-(N,N-Diisopropylcarboxamide)-A-nor-5α-androst-2-ene-phosphinic-acid

The title compound is prepared according to the procedure of Example 3(iii) by using 17β-N,N-diisopropyl-carboxamide-2-trifluoromethylsulfonate-A-nor-5α-androst-2-ene in place of 17β-N,N-diisopropylcarboxamide-3-tri-fluoromethylsulfonate-5α-androst-2-ene.

EXAMPLE 13

17β-(N,N-Diisopropylcarboxamide)-5α-androst-1,3-diene-3-phosphinic acid

The title compound is prepared according to Example 3 by substituting 3-oxo-5α-androst-1-ene-17β-N,N-diisopropylcarboxamide for 3-oxo-5α-androstane-17β-N,N-diisopropylcarboxamide.

EXAMPLE 14

(20R)-20-Carboxy-5α-Pregn-3-ene-3-Phosphinic acid

To a solution of 20α-(hydroxymethyl)-5α-pregn-3-ene-3-phosphinic acid prepared as in Example 10), (300 mg) in 25 ml acetone is added Jones reagent dropwise until a red color persists Isopropanol is then added to quench the excess oxidant. The solution is decanted from the gummy chromium salts, concentrated, and partioned between dichloromethane and water. The salts are dissolved in water and extracted with dichloromethane. The combined organic layers are then washed with brine, dried over sodium sulfate, and concentrated to yield (20R)-20-carboxy-5α-pregn-3-ene-3-phosphinic acid.

EXAMPLE 15

Androst-3,5-diene-17-one-3-phosphinic acid

The title compound is prepared by oxidation according to Example 14 of androst-3,5-diene-17β-ol-3phosphinic acid (described in Eur. J. Med. Chem. 10 (1975), p. 309).

EXAMPLE 16

Pregn-3,5,17(20)-triene-21-ethoxycarbonyl-3-phosphinic acid

A solution of sodium ethoxide (680 mg) in 5 ml ethanol is added to a mixture of androst-3,5-diene-17-one-3-phosphinic acid (950 mg), prepared as in Example 15, and methyl diethylphosphonoacetate (2.12 g), and the resulting mixture heated at reflux for 4 hours. The mixture is cooled, concentrated, diluted with dilute acetic acid and washed with ether. The combined ethereal extracts are washed with water and brine, and concentrated to yield the title compound.

EXAMPLE 17

Androst-3,5,16-triene-17-N,N-diisopropylcarboxamide-3-phosphinic acid (i)
Androst-3,5,16-triene-17-(trifluoromethylsulfonate)-3-phosphinic acid To a solution of androst-3,5-diene-17-one-3-phosphinic acid (320 mg), prepared as in Example 13, in 10 ml methylene chloride is added 2,6-di-t-butyl-4-methylpyridine (272 mg) and trifluoromethanesulfonic anhydride (0.3 ml) and the solution is stirred for 4 hours. The reaction mixture is then diluted with methylene chloride, washed with 10% hydrochloric acid, brine, and concentrated to yield crude androst-3,5,16-triene-17-(trifluoromethyl-sulfonate)-3-phosphinic acid.

(ii)
Androst-3,5,16-triene-17-N,N,diisopropylcarboxamide-3-phosphinic acid

A mixture of androst-3,5,16-triene-17-(trifluoromethylsulfonate)-3-phosphinic acid (450 mg), triethylamine (200 mg), diisopropylamine (4 g) and bis(triphenylphosphine)palladium(II) acetate (22 mg) in 4 ml DMF is stirred under an atmosphere of carbon monoxide for 4 hours. Th mixture is then diluted with 10% hydrochloric acid and thoroughly washed with dichlormethane. The dichloromethane solution is washed with brine, dried and concentrated, and the residue is recrystallized (diethylether) to yield androst-3,5,16-triene-17-N,N-diisopropylcarboxamide-3-phosphinic acid.

EXAMPLE 18

2,3'α-Tetrahydrofuran-2'-spiro-17-(3,5-androstadiene-3-phosphinic acid

The title compound is prepared according to Example 1 by substituting 2',3'α-tetrahydrofuran-2'-spiro-17-(androst-4-ene-3-one) for 17β-N,N-diisopropyl-carboxamide-androst-4-ene-3-one.

EXAMPLE 19

17β-acetamido-3,5-androstadiene-3-phosphinic acid.

The title compound is prepared according to Example 1 by substituting 17β-acetamido-4-androsten-3-one for 17β-N,N-diisopropylcarboxamide-androst-4-ene-3-one.

EXAMPLE 20

Androst-3,5-diene-17α-ol-17β-carboxy-3-phosphinic acid (i) 17β-Cyano-17α-acetoxyandrost-4-ene-3-one 4-Androsten-3,17-dione (20 g) is dissolved by gentle warming in acetone cyanohydrin (30 ml). The crystals which form after several minutes are filtered, washed with pentane, and then dissolved in a mixture of pyridine (50 ml) and acetic anhydride (50 ml). After 48 hours the volatiles are removed under reduced pressure. The residue is then dissolved in ether and washed successively with 5% hydrochloric acid and aqueous sodium bicarbonate. The organic solution is dried and concentrated to afford a mixture of C-17 epimers of 17-cyano-17-acetoxyandrost-4-ene-3-one. Chromatography affords 17β-Cyano-17α-acetoxyandrost-4-ene-3-one.

(ii)
17β-cyano-17α-acetoxy-androst-3,5-diene-3phosphinic acid

The title compound is prepared according to Example 1 by substituting 17-cyano-acetoxyandrost-4-ene-3-one for 17β-N,N-diisopropylcarboxamide-androst-4-ene-3-one.

(iii)
Androst-3,5-diene-17α-ol-17β-Carboxy-3-phosphinic acid

A solution of 17β-cyano-17α-acetoxy-androst-3,5-diene-3-phosphinic acid in methanol is cooled to 15° C. Dry hydrochloric acid is bubbled into the solution and the mixture allowed to stand at room temperature for 2 hours. Solvent is then removed under reduced pressure. A mixture of 1:1 THF-water is added followed by excess sodium hydroxide and the mixture is stirred or 2 hours. The reaction mixture then is acidified and extracted with chloroform. Concentration of the organic solution affords androst-3,5-diene-17β-ol-17β-carboxy-3-phosphinic acid.

EXAMPLE 21

17β-N,N-Diisopropylcarboxamide-andorst-3,5,7-triene-3-phosphinic acid

.(i)
Androst-4,6-diene-3-one-17β-N,N-diisopropylcarboxamide

Androst-4-ene-3-one-17β-N,N-diisopropylcarboxamide (12 g, 30 mmol) and chloranil (8.95 g, 36.4 mmol) in 700 ml t-butanol is heated at reflux for 3.5 hours, then cooled and filtered. The filtrate is concentrated and the residue taken up in 700 ml trichloromethane and washed successively with 4×150 ml water, 3×150 ml aqueous sodium bicarbonate, 3×150 ml 5% sodium hydroxide, 3×150 ml brine, dried over sodium sulfate and concentrated to yield androst-4,6-diene-3-one-17β-N,N-diisoproplycarboxamide.

(ii) 17 β-N,N-Diisopropylcarboxamide-androst-3,5,-triene-3-phosphinic acid

The title compound is prepared according to Example 1 (iii) by substituting 17β-N,N-diisopropylcarboxamide-androst-4-ene-3-one.

EXAMPLE 22

A-Homo-5α-androst-4-ene-17β-N,N-diisopropylcarboxamide-4-phosphinic acid (i) A-Homo-5α-androstan-4-ene-17β-N,N-diisopropylcarboxamide To a 0° C. solution of 3-oxo-5α-androstane-17β-N,N-diisopropylcarboxamide (15 g), prepared as in Example 5, and KOH (28 g) in ether (500 ml) and methanol (850 ml) is added 20 g of N-methylnirrosourea over 20 minutes. After 5 hours, 300 ml of 10% hydrochloric acid is added and the mixture is filtered and concentrated to remove the organiz solvents. The resulting aqueous suspension is extracted with ether and ethereal solution is dried and concentrated. Chromatography of the residue yields A-homo-5α-androstane-4-one-17β-N,N-diisopropylcarboxamide.

(ii) A-Homo-5α-androst-4-ene-17β-N,N-diisopropyl-carboxamide-4-phosphinic acid

Utilizing the protocol of Example 1, substitution of 17β-N,N-diisopropylcarboxamide-androst-4-ene-3-one with A-homo-5α-androstane-4-one-17β-N,N-diisopropylcarboxamide yields a mixture of 3-ene, and 4-ene A-homo-4-phosphinic acids. Chromomatography and recrystallization yields pure A-homo-5α-androst-4-ene-17β-N,N-diisopropylcarboxamide-4phosphinic acid.

EXAMPLE 23

17β-N,N-Diisopropylcarboxamide-4-chloro-androst-3,5-diene-3-phosphinic acid (i) 3-Qxo-androstane-4,5-a-epoxide-17β-N,N-diisopropylcarboxamide The title compound is prepared according to Example 11 (ii)) by substituting androst-4-ene-3-one-17β-N,N-diisopropylcarboxamide for 3-oxo-5α-androst-1-ene-β-N,N-diisopropylcarboxamide.

(ii) 3-Oxo-4-chloro-4-androstene-17β-N,N-diisopropylcarboxamide

A stream of hydrogen chloride gas is passed through a chloroform solution of 3-oxo-androstane-4,5α-epoxide-17β-N,N-diisopropylcarboxamide for 2 minutes. The solution is then washed with water, dried (Na$_2$SO$_4$), and concentrated to yield 3-oxo-4-chloro-4-androstene-17β-N,N-diisopropylcarboxamide.

(iii) 17β-N,N-Diispropopylcarboxamide-4-chloroandrost-3,5-diene-3-phosphinic acid.

The title compound is prepared according to Example 1 by substituting 3-oxo-4-chloro-4-androstene-17β-N,N-diisopropylcarboxamide for 17β-N,N-diisopropylcarboxamide-androst-4-ene-3-one.

EXAMPLE 24

17β-N,N-Diisopropylcarboxamide-4-methyl-5α-androst-3-ene-3-phosphinic acid (i) 3-Oxo-17β-N,N-Diisopropylcarboxamido-4-methyl-4-androstene A mixture of potassium-t-butoxide (5 g) in 100 ml t-butanol is heated to reflux. A solution of 3-oxo-17β-(N,N-diisopropylcarboxamido)-4-androstene (10 g) in t-butanol is added followed by a solution of methyl iodine (2.7 g) in t-butanol. Heating is continued for 3 hours. The mixture is then cooled, acidified, and extracted with dichloromethane. The di%hlOrOmethane solution is washed with brine, dried, and concentrated to yield 3-oxo-17β-(N,N-diisopropylcarboxamido)-4-methyl-4-androstene.

(ii) 17β-N.N-Diisopropylcarboxamide-4-methyl-5α-androst-3-ene-3-phosphinic acid

The title compound is prepared according to Example 5 by substituting 3-oxo-17B-(N,N-diisopropyl-carboxamido)-4-methyl-4-androstene for 3-oxo-17B-(N,N-diisopropylcarboxamido)-4-androstene.

EXAMPLE 25

17β-N.N-Diisopropylcarboxamide-4-trifluoromethyl-androst-3,5-diene-3-phosphinic acid (i) 3-Oxo-4-trifluoromethyl-4-androstene-17β-N,N-diisopropylcarboxamide A solution of 3-oxo-4-androstene-17β-N,N-diisopropylcarboxamide (1 g) in 10 ml of pyridine is cooled to −78° C. Trifluoromethyl iodide gas is condensed in a dry ice-acetone bath and added to the steroidpyridine cooled solution. The resulting solution is photolyzed using a medium pressure 450 watt mercury vapor lamp at room temperature for 18 hours. The reaction mixture is then diluted with ethyl acetate, washed with cold dilute hydrochloric acid, 5% sodium bisulfite, water, brine, dried over anhydrous sodium sulfate, and concentrated to dryness. Purification on a silica gel column eluting with 20% ethyl acetate in hexane yields 3-oxo-4-trifluoromethyl-4-androstene-17β-N,N-diisopropylcarboxamide.

(ii) 17β-N,N-diisopropylcarboxamide-4-trifluoromethyl-androst-3,5-diene-3-phosphinic acid The title compound is prepared according to Example 1 by substituting 3-oxo-4-trifluromethyl-4-androstene-17β-N,N-diisopropylcarboxamide for 17β-N,N-diisopropylcarboxamide-androst-4-ene-3-one.

EXAMPLE 26

17β-N,N-Diisopropylcarboxamide-6-trifluoromethyl-androst-3,5-diene-phosphinic acid (i) 3-Oxo-6-trifluromethyl-4-androstene-17β-N,N-diisopropylcarboxamide 17β-N,N-diisopropylcarboxamide-3-(trifluoromethylsulfonate)-androst-3,5-diene (1 g) is dissolved in 10 ml of pyridine and is photolyzed using a Hanovia medium pressure 450 watt mercury lamp at room temperature for 18 hours. The reaction solution is diluted with ethyl acetate which in turn is washed with cold dilute hydrochloric acid, water brine, dried over anhydrous magnesium sulfate, and evaporated to dryness. Silica gel column chromatography eluting with 20% ethyl acetate in hexane affords 3-oxo-6-trifluoromethyl-4-androsten-17β-N,N-diisopropylcarboxamide.

(ii)
17β-N,N-Diisopropylcarboxamide-6-trifluoromethyl-androst-3,5-diene-3-Phosphinic acid The title compound is prepared according to Example 1 by substituting 3-oxo-6-trifluoromethyl-4-androstene-17β-N,N-diisopropylcarboxamide for 17β-N,N-diisopropylcarboxamide-andorst-4-ene-3-one.

EXAMPLE 27

17β-N,N-Diisopropylcarboxamide-6-fluoro-androst-3,5-diene-3-phosphinic acid (i)
17β-N,N-Diisopropylcarboxamide-5-androstene-3-soiro-2'-dioxolane To a solution of 3-oxo-4-androstene-17β-N,Ndiisopropylcarboxamide (8g) in 300 ml of benzene was added 30 ml of ethlene glycol and p-toluenesulfonic acid (240 mg). The resulting solution was refluxed under argon with water collecting using a Dean Stark trap for 30 hours. The reaction mixture was then allowed to cool to room temperature and diluted with ethyl acetate. The organic layer was washed with 5% sodium bicarbonate, brine, dried over anhydrous magnesium sulfate, and evaporated to dryness. The crude material was purified on a silica gel column using 20% ethyl acetate in hexane as the eluting solvent to afford 7 g of 17β-N,N-diisopropylcarboxamide-5-androstene-3-spiro-2'-dioxolane (80%).

(ii)
17β-N,N-Diisopropylcarboxamide-5-6α-epoxy-androstane-3-soiro-2'-dioxolane

To a solution of 17β-N,N-diisopropylcarboxamide-5-androstene-3-spiro-2'-dioxolane (4.43 g, 10 mmol) in 100 ml of dry dichloromethane at 0° C. was added a solution of m-chloroperbenzoic acid (2.8 g) in 40 ml of dichloromethane dropwise through a dropping funned. After completion ofaddition of m-chloroperbenzoic acid (2.8 g) in 40 ml of dichloromethane dropwise through a dropping funnel. After completion of addition of m-chloroperbenzoic acid, the reaction mixture was allowed to warm to room temperature and stirred for another 30 minutes. The reaction mixture was then washed with 10% aqueous sodium sulfite solution four times followed by 5% aqueous sodium bicarbonate solution, brine, dried over anhydrous magnesium sulfate, and concentrated to a syrup. Column chromatography, eluting with 30% ethyl acetate in hexane, yielded 2.76 g of 17β-N,N-diisopropylcarboxamide-5,6α-epoxy-androstane-3-spiro-2'-dioxolane as a white solid (61%).

(iii)
3-Oxo-6-fluoro-4-androstene-17β-N,N-diisopropylcarboxamide

17β-N,N-diisopropylcarboxamide-5α,6α-epoxy-androstane-3-spiro-2'dioxolane (2.5 g) was dissolved in a mixture of 50:50 (v/v)benzene and ether. To this solution was added borontrifluoride-etherate (2.5 ml) under argon. The reaction solution was stirred at room temperature under argon for four hours and then quenched with 5% aqueous sodium carbonate. The organic layer was washed with water, brine, dried over anhydrous magnesium sulfate, and evaporated to dryness under reduced pressure. The residue was then treated with 15 ml of saturated hydrogen chloride in glacial acetic acid. The resulting solution was stirred at room temperature under argon for 1.5 hours and then diluted with ethyl acetate. The ethyl acetate solution was washed with 5% aqueous sodium bicarbonate, water, brine, dried over anhydrous magnesium sulfate, and evaporated to dryness. The crude material was purified on a silica gel column eluting with 25% ethyl acetate in hexane to yield 3-oxo-6β-fluoro-4-androstene-17β-N,N-diisopropylcarboxamide (675 mg, 30%) and 3-oxo-6α-fluoro-4-androstene-17β-N,N-diisopropylcarboxamide (900 mg, 40%).

(iv)
17β-N,N-Diisopropylcarboxamide-3-(trifluoromethylsulfonate)-6-fluoro-androst-3,5-diene To a solution of the empimers of 3-oxo-6-fluoro-4-androstene-17β-N,N-diisopropylcarboxamide (1.4 g) in 50 ml of dry dichloromethane was added 2,6-di-t-butyl-4methylpyridine (850 mg) followed by trifluoromethanesulfonic anhydride (0.75 ml) under argon. The resulting solution was stirred at room temperature under argon for 3 hours. The solvent was then removed under reduced pressure. The residue was redissolved in ethyl acetate which in turn was washed with cold dilute hydrochloric acid, water, brine, dried over anhydrous magnesium sulfate, and evaporated to an oil. Column chromatography (silica gel, 10% ethyl acetate in hexane) yielded 17β-N,N-diisopropYlcarboxamide-3-(trifluoromethylsulfonate)6-fluoroandrost-3,5-diene and 17β-N,N-diisopropyl-carboxamide-3-(trifluoromethylsulfonate)-6-fluoroandrost-2,4-diene.

(v)
17β-N,N-Diisopropylcarboxamide-6-fluoroandrost-3,5-diene-3-phosphinic acid

The title compound is prepared according to Example 3 (viii) by substituting 17β-N,N-diisopropylcarboxamide-3-(trifluoromethylsulfonate)-6-fluoroandrost2,4-diene for 17β-N,N-diisopropylcarboxamido-3-(trifluoromethylsulfonate)-5α-androst-2-ene.

EXAMPLE 28

17β-N,N-diisopropylcarboxamideandrost-2-ene-3-methylphosphinic cid

The title compound is prepared according to Example 9 by substituting 17β-N,N-diisopropyl-carboxamide-3-trifluoromethylsulfonate-5α-androst-2ene (prepared as in Example 7) in place of 17β-N,N-diisopropylcarboxamide-3-trifluoromethylsulfonate-androst3,5-diene.

EXAMPLE 29

17β-N,N-Diisopropylcarboxamide-5α-androstane-3-phosphinic acid

17β-N,N-diisopropylcarboxamido-androst-2-ene-3phosphinic acid (100 mg) is shaken in a Parr apparatus in 20 mL of a 3:1 solution of ethyl acetate in acetic acid at 25° C. and 1 atm of hydrogen over 30 mg of 10% of palladium on charcoal. The suspension is filtered, the filtrate concentrated and the residue azeotroped with t-butanol to yield the title compound.

EXAMPLE 30

17β-N,N-Diisopropyl carboxamide-estr-3,5(10)-diene-3-phosphinic acid

(i) 3-Methoxy-estr-1.3.5(10).16-tetraene-17-N,N-diisopropylcarboxamide

The title compound was prepared by using methyl estrone in place of 17β-N,N-diisopropylcarboxamide-androst-4-ene-3-one in the procedure of Example 9(i) and treating the resulting 17-trifluoromethylsulfonate in DMF with diisopropylamine, bis(triphenylphosphine)palladium (II) acetate, triethylamine and carbon monoxide.

(ii) 3-Methoxy-estr-1,3,5(10)-triene-17β-N,N-diisopropylcarboxamide

3-Methoxy-estr-1,3,5(10) - triene-17β-N,N-diisopropylcarboxamide (4.45 g, 11.3 mmol) in 100 ml of a 3:1 solution of ethyl acetate and ethanol was hydrogenated at 25° and 1 atm over $PtO_2$ (350 mg) for 6 hours. The solution was filtered to remove the catalyst and concentrated to afford 4.36g (98%) of the title compound.

(iii) 3-Oxo-estr-5(10)-ene-17β-N,N-diisopropylcarboxamide

To a solution of 3-methoxyestr-1,3,5(10)-triene-17β-N,N-diisopropylcarboxamide (1.4 g, 3.5 mmol) in liquid ammonia (25 ml), THF (10 ml), and t-butanol (10 ml) at −33° C. was added 0.5 g of lithium wire. The solution was stirred for 5 hours and then methanol (10ml) was slowly added. The ammonia was allowed to evaporate and the residue was then partitioned between water and chloroform. The organic phase was concentrated to a white solid which was suspended in a methanol-water mixture and then treated with 1.4g oxalic acid for 1.5 hours. The reaction mixture was then diluted with water and extracted with ethyl acetate. The organic phase was concentrated and the residue chromatographed (silica, 1:9 ethyl acetate-hexane) to yield 0.4g of the title compound.

(iv) 17β-N,N-Diisopropylcarboxamide-estr-3.5-(10)-diene-3-phosphinic acid

The title compound is prepared according to Example 3 by using 3-oxo-estr-5(10)-ene-17β-N,N-diisopropylcarboxamide for 3-oxo-5α-androstane-17β-N,N-diisopropylcarboxamide.

EXAMPLE 31

17β-N-N-Diisopropylcarboxamide-estr-3,5-diene phosphinic acid

(i) 3-Oxo-estr-4-ene-17β-N,N-diisopropylcarboxamide 3-oxo-estr-5(10)-ene-17β-N,N-diisopropylcarboxamide (Example 30 iii) was dissolved in methanol aqueous HCl (2:1) and heated at 65° for 1 hour, cooled and thoroughly extracted with chloroform. The organic extracts were concentrated to yield the title compound as a white solid.

(ii) 17β-N,N-Diisopropylcarboxamide-estr-3,5-diene-3-phosphinic acid

The title compound is prepared according to Example 1 (ii and iii) by using 3-oxo-estr-4-ene-17β-N,N-diisopropylcarboxamide in place of 17β-N,N-diisopropyl-carboxamide-androst-4-ene-3-one.

EXAMPLE 32.

17β-(N,N-Diisopropylcarboxamide)-androst-3.5.11-triene-3-phosphinic acid

(i) Androst-4-ene-3-one-11-ol-17β carboxylic acid

Corticosterone is dissolved in methanol and treated with an aqueous solution of periodic acid at room temperature for 18 hours. The solution is then diluted with water to induce precipitation of androst-4-ene-3-one-11-ol-17β-carboxylic acid which is collected by filtration.

(ii) Androst-4-ene-3.11-dione-17β-carboxylic acid

To a solution of androst-4-ene-3-one-11-ol-17β-carboxylic acid in acetone is added Jones Reagent dropwise until a red persists. Isospropanol is then added to quench the excess oxidant. The solution is decanted and the residual chromium salts are thoroughly washed with acetone. The combined organic solutions are then filtered through magnesium sulfate and concentrated to yield androst-4-ene-3,11-dione-17β-carboxylic acid.

(iii) Androst-4-ene-3,11-dione-17β-(N,N-diisopropylcarboxamide)

The title compound is prepared according to Example 1(ii) by substituting androst-4-ene-3,11-dione-17β-carboxylic acid for androst-4-ene-3-one-17β-carboxylic

(iv) 17β-(N,N-Diisopropylcarboxamide)-3-(trifluoromethylsulfonate)-11-oxo-androst-3,5-diene The title compound is prepared according to Example 26 (i) by substituting androst-4-ene-3,11-dione-17β-(N,N-diisopropylcarboxamide) for androst-4-ene-3-one-17β-(N,N-diisopropylcarboxamide).

(v) 17β-N,N-diisopropylcarboxamide-11-oxo-androst-3.5-diene-3-phosphinic acid The title compound is prepared according to Example 9 by substituting 17β-(N,N-diisopropylcarboxamide)-3-(trifluoromethylsulfonate)-11-oxo-androst-3,5-diene for 17β-(N,N-diisopropylcarboxamide)-3-(trifluoromethylsulfonate)-androst-3,5-diene and hypophosphorous acid for methylphosphinic acid methyl ester.

(vi) 17β-N,N-diisopropylcarboxamide-11-(trifluoromethylsulfonate)-androst-3,5,11-triene-3-phosphinic acid The title compound is prepared according to Example 9(i) using 17β-(N,N-diisopropylcarboxamide)-11-oxo-androst-3,5-diene-3-phosphinic acid.

(vii)
17β-N,N-diisopropylcarboxamide-androst-3,5,11-triene-3-phosphinic acid

The title compound is prepared according to the procedure of Cacchi (Tet. Lett. 25 (42) 4821–4824 (1984)) by substituting 17β-N,N-diisopropylcarboxamide-11-trifluoromethylsulfonate)-androst-3,5,11-triene-3phosphinic acid.

EXAMPLE 33

17β(N-t-Butylcarboxamide)-androst-3,5,11-triene-3-phosphinic acid

The process of Example 32 wherein N-t-butylamine is used in place of diisopropylamine yields 17β-N-t-butylcarboxamide-androst-3,5,11-triene-3-phosphinic acid.

EXAMPLE 34–39

The following compounds are prepared by substituting t-butylamine for diisopropylamine using the procedures of examples 9, 11, 13, 29, 30, and 31 respectively:
34. 17β-N-t-Butylcarboxamide-4-fluoro-5α-androst-3-ene-3-phosphinic acid;
35. 17β-N-t-Butylcarboxamide-5α-androst-1,3-diene-3-phosphinic acid;
36. 17β-N-t-Butylcarboxamide-androst-3,5-diene-3-methylphosphinic acid;
37. 17β-N-t-Butylcarboxamide-5α-androstane-3phosphinic acid;
38. 17β-N-t-Butylcarboxamide-estr-3,5(10)-diene-3-phosphinic acid; and
39. 17β-N-t-Butylcarboxamide-estr-3,5-diene-3phosphinic acid.

EXAMPLE 40

An oral dosage form for administering Formula (I) compounds is produced by screening, mixing, and filling into hard gelatin capsules the ingredients in the proportions shown in Table V, below.

TABLE V

| Ingredients | Amounts |
|---|---|
| 17β-N,N-diisopropylcarboxamide-androst-3,5-diene-3-phosphinic acid | 50 mg |
| magnesium stearate | 5 mg |
| lactose | 75 mg |

EXAMPLE 41

The sucrose, calcium sulfate dihydrate and Formula (I) compound shown in Table VI below are mixed and granualted in the proportions shown with a 10% gelatin solution. The wet granules are screened, dried, mixed with the starch, talc and stearic acid, screened and compressed into a tablet.

TABLE VI

| Ingredients | Amounts |
|---|---|
| 17β-N,N-Diisopropylcarboxamide-5α-androst-3-ene-3-phosphinic acid | 100 mg |
| calcium sulfate dihydrate | 150 mg |
| sucrose | 20 mg |
| starch | 10 mg |
| talc | 5 mg |
| stearic acid | 3 mg |

EXAMPLE 42

17β-N-t-Buty%carboxamide-androst-3,5-diene-3-phosphinic acid, 75 mg is dispersed in 25 ml of normal saline to prepare an injectable preparation.

While the preferred embodiments of the invention are illustrated by the above, it is to be understood that thte invention is not limited to the precise embodiments herein disclosed and that the right to all modifications coming within the scope of the following claim is reserved.

What is claimed is:

1. A compound represented by the formula:

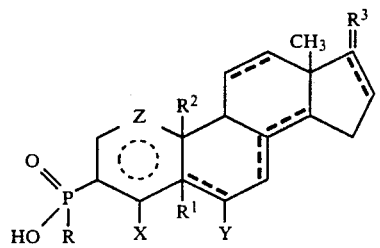

in which:

The A ring has up to 2 double bonds;

The B, C, and D rings have optional double bonds where indicated by the broken lines, provided that the A, B and C rings do not have adjacent double bonds;

R is hydrogen or $C_{1-4}$alkyl;

Z is $CH_2$ or, when part of a double bond, CH

X is H, F, Cl, Br, I, CF, or $C_{1-6}$alkyl;

Y is H, F, Cl, $CF_3$, or $CH_3$ provided that Y is H when there is no $C_5$–$C_6$ double bond;

$R^2$ is absent or present as H or $CH_3$ provided $R^2$ is absent when the carbon to which it is attached is double bonded;

$R^1$ is absent when there is a $C_4$–$C_5$, $C_5$–$C_6$ or $C_5$–$C_{10}$ double bond, or present as an alpha hydrogen; and $R^3$ is (1) α-hydrogen, α-hydroxyl, or α-acetoxy and/or

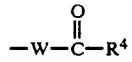

where W is a bond or $C_{1-12}$alkyl, and $R^4$ is (i) hydrogen,
(ii) hydroxy,
(iii) $C_{1-8}$alkyl;
(iv) $C_{1-8}$alkoxy;
(v) $N(R^5)$, where each $R^5$ is independently selected from hydrogen, $C_{1-8}$-alkyl, $C_{3-6}$-cycloalkyl, phenyl; or taken together with the nitrogen to which they are attached represent a 5–6 membered saturated ring comprising up to one other heteroatom selected from oxygen and nitrogen, or
(vi) $OR^6$, where $R^6$ is hydrogen, alkali metal, $C_{1-18}$-alkyl, benzyl, or (b) Alk-$OR^7$, where Alk is $C_{1-12}$-alkyl, and $R^7$ is
(i) phenyl-$C_{1-16}$alkylcarbonyl,
(ii) $C_{5-10}$cYcloalkylcarbonyl,
(iii) benzoyl,
(iv) $C_{1-18}$alkoxycarbonyl, (v) aminocarbonyl or $C_{1-8}$-alkyl substituted aminocarbonyl,
(vi) hydrogen, or
(vii) $C_{1-8}$-alkyl,
(2) =CH—W—COR$^4$ or =CH—W—OR$^7$, where W is a bond or $C_{1-12}$alkylidene, R$^4$ and R$^7$ have the same meaning as above and R$^7$ also is hydrogen or $C_{1-20}$-alkylcarbonyl;
(3)

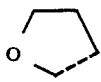

where the dashed bond replaces the 17α-hydrogen,
(4) α-hydrogen and NHCOR$^8$ where R$^8$ is $C_{1-12}$alkyl or $N(R^5)_2$ where R$^5$ has the same meaning as above,
(5) α-hydrogen and cyano,
(6) α-hydrogen and tetrazolyl, or
(7) keto;
or a pharmaceutically acceptable salt thereof.

2. A compound of claim 1 in which R$^3$ is N,N-diisopropylcarboxamide or N-t-butylcarboxamide.

3. A compound of claim 1 having the following formula

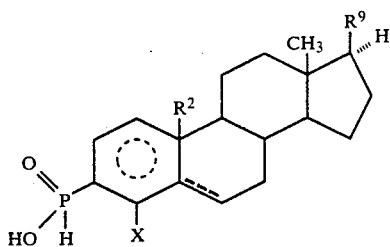

in which:
The A ring has up to 2 double bonds;
The B ring has an optional double bond where indicated by the broken line and provided that the A and B rings do not have adjacent double bonds;
X is H or halo,
R$^1$ is absent when there is a $C_4$–$C_5$, $C_5$–$C_6$, or $C_5$–$C_{10}$ double bond, or present as an alpha hydrogen; and
R$^9$ is
(a) $C(CH_3)Ch_2OR^{10}$ wherein R$^{10}$ is H or $C_{1-6}$alkyl, or
(b) $CON(R^{10})_2$ wherein R$^{20}$ is as defined above or a pharmaceutically acceptable salt thereof.

4. A compound of claim 4 wherein the A ring has a $C_3$–$C_4$ double bond.

5. A compound of claim 4 wherein R$^3$ is N,N-diisopropylcarboxamide or N-t-butylcarboxamide.

6. The compound of claim 3 that is 17β-N,N-diisopropylcarboxamide-5α-androst-3-ene-3-phosphinic acid or a pharmaceutically acceptable salt thereof.

7. The compound of claim 3 that is 17β-N,N-diisopropylcarboxamide-5α-androst-3,5-diene-3-phosphinic acid or a pharmaceutically acceptable salt thereof.

8. The compound of claim 3 that is 17β-N,N-diisopropylcarboxamide-5α-androst-2-ene-3-phosphinic acid or a pharmaceutically acceptable salt thereof.

9. The compound of claim 3 that is 17β-N,N-diisopropylcarboxamide-5α-androst-2,4-diene-3-phosphinic acid or a pharmaceutically acceptable salt thereof.

10. The compound of claim 1 that is 17β-N,N-diisopropylcarboxamide-androst-2,4-diene-3-phosphinic acid or a pharmaceutically acceptable salt thereof.

11. The compound of claim 3 that is 17β-N,-t-butylcarboxamide-androst-3,5-diene-3-phosphinic acid or a pharmaceutically acceptable salt thereof.

12. A compound represented by the formula:

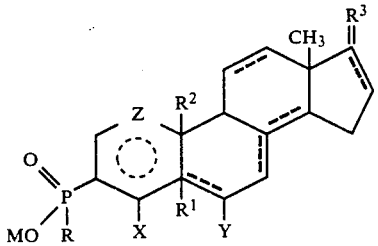

in which:
The A ring has up to 2 double bonds;
The B, C, and D rings have optional double bonds where indicated by the broken lines, provided that the A, B, and C rings do not have the adjacent double bonds;
M is $C_{1-8}$alkyl;
R is hydrogen or $C_{1-4}$alkyl;
Z is $CH_2$or, when part of a double bond, CH.
X is H, F, Cl, Br, I, $CF_3$, or $C_{1-6}$alkyl;
Y is H, F, Cl, $CF_3$, or $CH_3$, provided that Y is H when there is no $C_5$–$C_6$ double bond;
R$^2$ is absent or present as H or $CH_3$, provided R$^2$ is absent when the carbon to which it is attached is double bonded;
R$^1$ is absent when there is a $C_4$–$C_5$, $C_5$–$C_6$, or $C_5$–$C_{10}$ double bond, or present as an alpha hydrogen; and
R$^3$ is
(1) α-hydrogen, %-hydroxyl, or %-acetoxy and/or
(a)

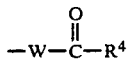

where W is a bond or $C_{1-12}$alkYl and R$^4$ is
(i) hydrogen,
(ii) hydroxyl,
(iii) $C_{1-8}$alkyl,
(iv) $C_{1-8}$alkoxy,
(v) $N*(R^5)_2$, where each R$^5$ is independently selected from hydrogen, $C_{1-8}$-alkyl, $C_{3-6}$cycloalkyl, phenyl; or taken together with the nitrogen to which they are attached represent a 5-6 membered saturated ring comprising up to one other heteroatom selected from oxygen and nitrogen, or
(vi) OR$^6$, where R$^6$ is hydrogen, alkali metal, $C_{1-18}$-alkyl, benzyl, or
(b) Alk-OR$^7$, where Alk is $C_{1-12}$-alkyl, and R$^7$ is
(i) Phenyl-$C_{1-6}$alkylcarbonyl, $C_{5-10}$-cycloalkylcarbonyl,
(iii) benzoyl,
(iv) $C_{1-8}$-alkoxycarbonyl,
(v) aminocarbonyl, or $C_{1-8}$ alkyl substituted aminocarbonyl (vi) hydrogen, or
(vii) $C_{1-8}$-alkyl, (2) =CH—W—CO—$R^4$ or =CH—W—$OR^7$, where W is a the same meaning as above and $R^7$ also is hydrogen or $C_{1-20}$-alkylcarbonyl;

(3)

where the dashed bond replaces the 17α-hydrogen,

α-hydrogen and NHCOR$^8$ where R$^8$ is $C_{1-12}$alkyl or N(R$^5$)$_2$ where R$^5$ has the same meaning as above, (5) α-hydrogen and cyano,
(6) α-hydrogen and tetrazolyl, or
(7) keto; or a pharmaceutically acceptable salt thereof.

13. A compound of claim 8 wherein R is methyl.

14. A compound of claim 12 that is 17β-N,N-diisopropylcarboxamide-androst-3,5-diene-3-methylphosphinic acid methyl ester.

15. A pharmaceutical composition comprising a compound of claim 1 and a pharmaceutically acceptable carrier.

16. A composition of claim 15 wherein the compound is 17β-N,N-diisopropylcarboxamide-5α-androst-3-ene-3-phosphinic acid or a pharmaceutically acceptable salt thereof.

17. A composition of claim 15 wherein the compound is 17β-N,N-diisopropylcarboxamide-androst-3,5-ene-3-phosphinic acid or a pharmaceutically acceptable salt thereof.

18. A composition of claim 15 wherein the compound is 17β-N,N-diisopropylcarboxamide-androst-3,5-ene-3-phosphinic acid or a pharmaceutically acceptable salt thereof.

19. A method of inhibiting steroid 5α-reductase activity in mammals which comprises administering to a subject an effective amount of a compound of claim 1.

20. A method of reducing or maintaining prostate size in mammals which comprises administering to a subject an effective amount of a compound of claim 1.

* * * * *

UNITED STATES PATENT AND TRADEMARK OFFICE
CERTIFICATE OF CORRECTION

PATENT NO. : 5,026,882
DATED : June 25, 1991    Page 1 of 3
INVENTOR(S) : Holt, Levy, Metcalf It is certified that error appears in the above-identified patent and that said Letters Patent is hereby corrected as shown below:

In Claim 1, column 38, line 45; change "
$$-W-\overset{\overset{O}{\|}}{C}-R^4$$
"

to --- (a)
$$-W-\overset{\overset{O}{\|}}{C}-R^4$$
---.

In Claim 4, column 39, line 55; change "A compound of Claim 4 wherein" to --- A compound of Claim 3 wherein ---.

In Claim 5, column 39, line 57; change "5. A compound of Claim 4 wherein $R^3$ is" to --- 5. A compound of Claim 3 wherein $R^3$ is ---.

In Claim 7, column 39, line 64; change "propylcarboxamide-5α-androst" to --- propylcarboxamide-androst ---.

In Claim 8, column 39, lines 66 and 67; change "17ß-N,N-diisopropylcarboxamide-5α-androst" to --- 17ß-(N,N-diisopropylcarboxamide)-5α-androst ---.

In Claim 9, column 40, lines 1 and 2; change "17ß-N,N-diisopropylcarboxamide-5α-androst" to --- 17ß-(N,N-diisopropylcarboxamide)-androst ---.

UNITED STATES PATENT AND TRADEMARK OFFICE
CERTIFICATE OF CORRECTION

PATENT NO. : 5,026,882
DATED : June 25, 1991
INVENTOR(S) : Holt, Levy, Metcalf

It is certified that error appears in the above-indentified patent and that said Letters Patent is hereby corrected as shown below:

In Claim 10, column 40 line 5; change "propylcarboxamide-androst-2,4-diene-3-phosphinic" to --- propylcarboxamide-5α-androst-3,5-diene-3-methylphosphinic ---.

In Claim 12, column 40, line 41; change "%-hydroxyl, or %-acetoxy" to --- α-hydroxyl, or α-acetoxy ---.

In Claim 12, column 41, lines 4 and 5; change "where W is a the same meaning as above and $R^7$ also is hydrogen" to --- where W is a bond or $C_{1-12}$ alkylidene, and $R^4$ and $R^7$ have the same meaning as above and $R^7$ also is hydrogen ---.

UNITED STATES PATENT AND TRADEMARK OFFICE
CERTIFICATE OF CORRECTION

PATENT NO.  : 5,026,882
DATED       : June 25, 1991
INVENTOR(S) : Holt, Levy, Metcalf It is certified that error appears in the above-indentified patent and that said Letters Patent is hereby corrected as shown below:

In Claim 17, column 42, line 12; change "17ß-N,N-diisopropylcarboxamide-androst-3,5-ene-3" to --- 17ß-(N,N-diisopropylcarboxamide)-androst-3,5-diene-3 ---.

In Claim 18, column 42, line 16; change "17ß-N,N-diisopropylcarboxamide-androst-3,5-ene-3" to --- 17ß-N-t-butylcarboxamide-androst-3,5-diene-3.

Signed and Sealed this

Thirteenth Day of July, 1993

Attest:

MICHAEL K. KIRK

Attesting Officer

Acting Commissioner of Patents and Trademarks